United States Patent
Collins et al.

(10) Patent No.: US 8,391,574 B2
(45) Date of Patent: Mar. 5, 2013

(54) METHOD AND SYSTEM OF COMPUTER-AIDED QUANTITATIVE AND QUALITATIVE ANALYSIS OF MEDICAL IMAGES FROM MULTIPLE MODALITIES

(75) Inventors: Jeffrey Collins, Bellfountain (CA);
Frederic Lachmann, Toronto (CA);
Karen Saghatelyan, Toronto (CA);
Sandra Stapleton, Los Altos, CA (US)

(73) Assignee: The Medipattern Corporation, Toronto (CA)

( * ) Notice: Subject to any disclaimer, the term of this patent is extended or adjusted under 35 U.S.C. 154(b) by 0 days.

(21) Appl. No.: 13/182,132

(22) Filed: Jul. 13, 2011

(65) Prior Publication Data

US 2011/0268338 A1 Nov. 3, 2011

Related U.S. Application Data

(63) Continuation of application No. 11/603,236, filed on Nov. 22, 2006, now Pat. No. 8,014,576.

(60) Provisional application No. 60/738,999, filed on Nov. 23, 2005.

(51) Int. Cl.
*G06K 9/00* (2006.01)

(52) U.S. Cl. ...................................................... 382/128

(58) Field of Classification Search ........................ None
See application file for complete search history.

(56) References Cited

U.S. PATENT DOCUMENTS

| | | | |
|---|---|---|---|
| 5,235,510 A | 8/1993 | Yamada et al. |
| 5,491,627 A | 2/1996 | Zhang et al. |
| 5,684,889 A | 11/1997 | Chen et al. |
| 5,790,690 A | 8/1998 | Doi et al. |
| 5,828,774 A | 10/1998 | Wang |
| 5,848,198 A | 12/1998 | Penn |
| 5,984,870 A | 11/1999 | Giger et al. |
| 6,009,342 A | 12/1999 | Brasch et al. |
| 6,054,990 A | 4/2000 | Tran |
| 6,058,322 A | 5/2000 | Nishikawa et al. |
| 6,091,841 A | 7/2000 | Rogers et al. |
| 6,138,045 A | 10/2000 | Kupinski et al. |
| 6,167,146 A | 12/2000 | Rogers et al. |
| 6,263,092 B1 | 7/2001 | Roehrig et al. |
| 6,301,378 B1 | 10/2001 | Karssemeijer et al. |

(Continued)

FOREIGN PATENT DOCUMENTS

| | | |
|---|---|---|
| CN | 1628611 A | 6/2005 |
| EP | 0487110 A2 | 5/1992 |

(Continued)

OTHER PUBLICATIONS

Stavros, A. T. et al.; "Solid Breast Nodules: Use of Sonography to Distinguish between Benign and Malignant Lesions"; Radiology; 1995, 196:123-134.

(Continued)

*Primary Examiner* — Bhavesh Mehta
*Assistant Examiner* — Tahmina Ansari
(74) *Attorney, Agent, or Firm* — Ralph A. Dowell; Dowell & Dowell, P.C

(57) ABSTRACT

A system and method of computer aided analysis of medical images and detection of malignant lesions is described. Medical images obtained from multiple modalities are analyzed. Morphological features as well as temporal, i.e., kinetics features, are combined to compute a consolidated assessment of a possible lesion detected in the medical images. The system includes at least one kinetics module, which is capable of extracting kinetics features from a time sequence of MRI images or MRS data taken after administering a contrast enhancement agent to a patient. The consolidated assessment is presented to a user for confirmation or modification.

27 Claims, 11 Drawing Sheets

U.S. PATENT DOCUMENTS

| | | | |
|---|---|---|---|
| 6,477,262 | B2 | 11/2002 | Wang |
| 6,553,356 | B1 | 4/2003 | Good et al. |
| 6,577,752 | B2 | 6/2003 | Armato et al. |
| 6,632,177 | B1* | 10/2003 | Phillips et al. ............... 600/458 |
| 6,697,506 | B1 | 2/2004 | Qian et al. |
| 6,748,044 | B2 | 6/2004 | Sabol et al. |
| 6,757,415 | B1 | 6/2004 | Rogers et al. |
| 6,763,128 | B1 | 7/2004 | Rogers et al. |
| 6,785,410 | B2 | 8/2004 | Vining et al. |
| 6,799,066 | B2 | 9/2004 | Steines et al. |
| 7,466,848 | B2 | 12/2008 | Metaxas et al. |
| 2003/0095147 | A1* | 5/2003 | Daw ........................... 345/771 |
| 2003/0103665 | A1 | 6/2003 | Uppaluri et al. |
| 2004/0008876 | A1* | 1/2004 | Lure et al. .................... 382/128 |
| 2004/0101181 | A1 | 5/2004 | Giger et al. |
| 2004/0120558 | A1* | 6/2004 | Sabol et al. .................. 382/128 |
| 2004/0193036 | A1 | 9/2004 | Zhou et al. |
| 2004/0258291 | A1 | 12/2004 | Gustafson |
| 2004/0264749 | A1 | 12/2004 | Skladnev et al. |
| 2005/0010445 | A1* | 1/2005 | Krishnan et al. ............... 705/2 |
| 2005/0013471 | A1 | 1/2005 | Snoeren et al. |
| 2005/0049497 | A1* | 3/2005 | Krishnan et al. ............... 600/437 |
| 2005/0059876 | A1 | 3/2005 | Krishnan et al. |
| 2005/0107683 | A1 | 5/2005 | Mountford et al. |
| 2005/0113680 | A1 | 5/2005 | Ikeda et al. |
| 2006/0274928 | A1* | 12/2006 | Collins et al. ................. 382/132 |
| 2007/0003124 | A1 | 1/2007 | Wood et al. |
| 2007/0036402 | A1* | 2/2007 | Cahill et al. .................. 382/128 |
| 2007/0133852 | A1* | 6/2007 | Collins et al. ................. 382/128 |
| 2009/0268952 | A1* | 10/2009 | Schaffer et al. ............... 382/128 |

FOREIGN PATENT DOCUMENTS

| | | | |
|---|---|---|---|
| JP | 63311942 | A | 12/1988 |
| JP | 2001/511372 | A | 8/2001 |
| JP | 2002/200048 | | 7/2002 |
| JP | 2003/000575 | A | 1/2003 |
| JP | 2003/506797 | A | 2/2003 |
| JP | 2003/116838 | | 4/2003 |
| JP | 2004/105731 | A | 4/2004 |
| JP | 2005/124617 | | 5/2005 |
| WO | WO 99/05503 | A2 | 2/1999 |
| WO | WO 02/094097 | A1 | 11/2002 |
| WO | WO 03/067371 | A2 | 8/2003 |
| WO | WO 2004/029851 | A1 | 4/2004 |
| WO | WO 2005/079306 | A2 | 9/2005 |

OTHER PUBLICATIONS

Teifke, A.; "Outcome analysis and rational management of enhancing lesions incidentally detected on contrast-enhanced MRI of the breast"; AJR; 2003; 181:655-662.

Kumar, N.A. et al; "An Evaluation of the Utility of a Computer-Aided Diagnosis System for the Interpretation of Breast Masses Detected by MRI"; RSNA 2001; Paper No. 1194. (abstract only).

Niemeyer, T. et al.; "Comparison of automatic time curve selection methods for breast MR CAD"; Proc. SPIE Medical Imaging 2004: Image Processing; Fitzpatrick, J. Michael; Sonka, Milan., Eds.; 2004; 5370:785-790.

Penn, A.I. et al.;"Preliminary performance analysis of breast-MRI CAD system"; Proc. SPIE. Medical Imaging 2001: Image Processing; Sonka, Milan; Hanson, Kenneth M., Eds.; 2001; 4322:1944-1953.

Penn, A.I. et al.; "Discrimination of MR Images of Breast Masses using Fractal-Interpolation Function Models"; Acad Radiol.; 1999; 6:156-163.

Yeung, D et al.; "Human Breast Lesions: Characterization with Contrast-enhanced in Vivo Proton MR Spectroscopy—Initial Results"; Radiology; Jul. 2001; vol. 220, No. 1:40-46.

Gujar et al.; "Magnetic Resonance Spectroscopy"; Journal of Neuro-Opthalmology; vol. 25, No. 3; Sep. 2005; pp. 217 to 226.

Gill, Coralie; Search Report from corresponding PCT Application No. PCT/CA2006/001910; search completed Mar. 29, 2007.

Montes, Pau; Supplementary Search Report from corresponding European Application No. 06804765.3; search completed Nov. 5, 2010.

Montes, Pau; Supplementary Search Report from related European Application No. 06752744.0; search completed Nov. 15, 2010.

* cited by examiner

METHOD AND SYSTEM OF COMPUTER-AIDED QUANTITATIVE AND QUALITATIVE ANALYSIS OF MEDICAL IMAGES FROM MULTIPLE MODALITIES

CROSS-REFERENCE TO RELATED APPLICATIONS

The present application is a continuation of U.S. application Ser. No. 11/603,236 filed on Nov. 22, 2006 which claims priority from U.S. Provisional Application No. 60/738,999 filed on Nov. 23, 2005, both of which are incorporated herein by reference.

FIELD OF INVENTION

The invention relates generally to the field of computer-aided analysis of medical images and detection of suspicious abnormalities. In particular, the invention relates to a method and system for processing medical images obtained from multiple modalities, including analysis of kinetics as well as morphological features and automated detection of abnormalities in and analysis of medical images from multiple modalities.

BACKGROUND OF INVENTION

Magnetic resonance imaging (MRI) is emerging as a powerful tool for the imaging of breast abnormalities. In general, MRI provides a better characterization of the breast lesions than conventional imaging modalities due to rich soft-tissue contrast, thin-section and multiplanar capabilities.

Traditionally, lesion morphology is analyzed and classified to discriminate benign lesions from possible cancer tumors. For example, American College of Radiology (ACR) has over the years developed a set of characteristics and lexicon for use with Breast Imaging Reporting and Data systems (BI-RADS®). BI-RADS MRI lexicon suggests that the following morphological features are likely associated with benign lesions:

| | |
|---|---|
| Shape | rounded, oval or lobular |
| Margin | smooth |
| Mass enhancement | homogeneous, no contrast enhancement, non-enhancing internal septation |

On the other hand, the BI-RADS MRI lexicon suggests that the following features are likely describing the possibility of malignancy:

| | |
|---|---|
| Shape | irregular |
| Margin | spiculated |
| Mass enhancement | heterogeneous, rim enhancement, ductal enhancement |

Recently, considerable attention has been focused on contrast-enhanced MRI of breast lesions. Before or during the exam, a contrast enhancement agent is injected into a vein in a patient's arm. Typically, a gadolinium based contrast agent (e.g., Gd-DTPA) is used. The use of contrast agents tends to provide greater contrast between normal and abnormal tissues. The contrast enhancement stems from the fact that the growth and metastatic potential of tumors can be directly linked to the extent of surrounding angiogenesis. For a tumor to grow larger than a few millimeters in diameter, it requires the formation of blood vessels that will supply oxygen and nutrients necessary for survival. These new vessels proliferate in a disorganized manner and are poor quality, thus making them leaky and causing blood to pool around the tumor. The analysis of the signal from diffusible contrast agents aids in the detection and characterization of suspicious abnormalities in breasts.

Quantitative studies of the signal intensity over time (or "kinetics curve"), as time variation of level of enhancement and the kinetics (e.g., uptake and washout behaviors), suggest that a malignant lesion is likely an area that enhances rapidly, reaching their peak enhancement between one and three minutes post injection. Benign lesions enhance more slowly, with the peak enhancement occurring after several minutes.

The shape of a kinetics curve also can be a good indicator whether a lesion is malignant. Studies have found that kinetics curves describing a benign lesion tend to be straight or slightly curved (type I). For the curved type, the time-signal intensity continue to increase but the growth is generally slower and the curve is flattened in the late post-contrast period, because of saturation effects. On the other hand, kinetics curves that suggest or indicate malignancy show a plateau or a washout section. The plateau type (type II) shows an initial upstroke, after which enhancement is abruptly cut off, and the signal intensity plateaus in the intermediate and late post-contrast periods. The washout type (type III) shows an initial upstroke, after which enhancement is abruptly cut off, and the signal intensities decreases (washes out) in the intermediate post-contrast period (2-3 minutes after injection of contrast agent).

However, although the contrast-enhanced MRI method has achieved high levels of sensitivity (94%-100%), it provides only limited specificity levels (40%-95%). Here, sensitivity refers to true positive detection and specificity refers to false positive reduction. The low specificity levels are result of not only malignant lesions enhancement but also enhancement of the benign lesions, causing a number of unnecessary biopsies. Thus, the presence of enhancement alone cannot be used to differentiate benign from malignant lesions.

Benign lesions are regarded as results of aberrations of normal processes. For example, fibrocystic lesions are the most common benign disorder (40%-50%), fibroadenoma is the most frequent tumor in young and adolescent woman, and pappiloma is a low risk lesion. Other benign lesions include radial scar (sclerosis), which is a stellate lesion mimicking cancer, phyllodes tumor, and ductal hyperplasia.

Investigations of contrast MRI of breasts have demonstrated that not only did malignant lesion enhance, but also many benign lesions including fibroadenomas, fibrocystic changes and radial scars enhanced. Also, there may be malignant lesions, such as certain cases of infiltrating ductal carcinoma (IDC), infiltrating lobular carcinoma (ILC) or ductal carcinoma in situ (DCIS) that will not enhance rapidly but in which lesion morphology suggests the presence of malignancy. The belief is that the presence of contrast enhancement alone cannot be used to differentiate benign from malignant lesion.

Recently, attention has also been turned to magnetic resonance spectroscopy ("MRS") as a new technique for diagnosing cancer. MRS is a particular type of magnetic resonance detection technique. It provides chemical information by measuring concentrations or strengths of various marker chemicals, such as choline, in a suspected tumor. It is believed that the amount or concentration of marker chemicals provide information about the disease process in the area examined.

In general, signals obtained from MRS do not generate a scanned image. Instead, spectroscopic information of various chemicals is produced. More recently, it has been possible to obtain spectroscopic data from a well localized area. This allows the biochemical information obtained from MRS to be evaluated in relation to the localized area. However, correlating spectroscopic data with a scanned image is generally a difficult task in clinical environments.

The forgoing creates challenges for developing a system and method of analyzing medical images for discriminating between malignant and benign lesions, suitable for clinical needs. It is an object of the present invention to mitigate or obviate at least one of the above mentioned disadvantages.

SUMMARY OF INVENTION

The invention combines both quantitative and qualitative features to achieve an optimal discrimination of suspicious abnormalities, such as imaged breast lesions. Images and data from multiple modalities are processed and analyzed to extract the quantitative and qualitative information. Quantitative information can include kinetics information and biochemical information. Kinetics features can be extracted from a time sequence of image data, such as MRI image data. Biochemical information can be extracted from a spectroscopic analysis of MRS data. Morphological features can be extracted from MRI images, ultrasound images, x-ray images, or images of other modalities. A computer application program is provided for extracting quantitative and qualitative features from medical images and data and for combining results from quantitative and qualitative analysis to produce a consolidated result. The analysis of time course kinetics can be performed before or after the evaluation of the lesions morphology in post-contrast images. Optionally, the results from the first performed analysis are evaluated prior to performing the next analysis. In those cases, if results from the first performed analysis (for example, kinetics analysis) are clearly suggestive, the next analysis (for example, morphology analysis) is not performed. If the results from the analysis of one mode (for example, kinetics) are indeterminate or suggest benign lesion, a further analysis (for example, morphology) is performed.

In one aspect of the invention, a method of analyzing a plurality of medical image data of a region in an anatomy and detecting abnormalities in the region is provided. At least a set of the plurality of medical image data contain temporal information responsive to administering of a contrast enhancement agent. The method includes the steps of obtaining the plurality of medical image data, identifying from the plurality of medical image data a set of data points representing a possible lesion in the region, extracting from the plurality of medical image data features associated with the set of data points, the features including at least two sets of a set of morphological features, a set of kinetics characteristics of the temporal information, and a set of biochemical characteristics, computing an initial diagnostic assessment of the possible lesion from the at least two sets of features, and providing the initial assessment to a user for evaluation. The assessment is evaluated by incorporating the at least two sets of features in an evaluation process.

In a feature of this aspect of the invention, the method includes the further steps of receiving a modification to the at least two sets of features from the user, computing a modified assessment, and providing the modified assessment to the user for further evaluation. The modified assessment is computed by incorporating the modification in the computation.

In another feature of this aspect of the invention, the kinetics characteristics are extracted from a contrast variation curve corresponding to time-dependent local contrast variation in a subset of said set of data points. In a further feature, the kinetics characteristics include a classification of the contrast variation curve into one of continued enhancement, plateau and washout types.

In yet another feature of this aspect of the invention, the biochemical characteristics are extracted from a spectral analysis of an MRS subset of the set of data points. In a further feature, the biochemical characteristics include at least a concentration distribution of a marker chemical or relative strength of two or more marker chemicals obtained from a spectroscopic analysis.

In another aspect, there is provided a system for analyzing a plurality of medical image data of a region in an anatomy. At least a set of the plurality of medical image data contain temporal information responsive to administering of a contrast enhancement agent. The system includes an image data module for retrieving the plurality of medical image data, a morphology module for identifying a possible lesion in said medical image data and extracting and classifying morphological features associated with said possible lesion, a kinetic module, a spectroscopic analysis module, a consolidation decision engine, and a graphical user interface for displaying at least a portion of the plurality of medical image data along with an initial diagnostic assessment for user evaluation and modification. The kinetics module extracts from the plurality of medical image data kinetics characteristics of the temporal information associated with the possible lesion, the spectroscopic analysis module extracts from the plurality of medical image data biochemical characteristics relating to one or more marker chemicals, and the consolidation decision engine receives the morphological features from the morphology module, the kinetics characteristics of the temporal information from the kinetics module, and the biochemical characteristics from the spectroscopic analysis module, and computes the initial diagnostic assessment of the possible lesion from the morphological features, the kinetics characteristics and the biochemical characteristics.

In a feature of this aspect of the invention, the system further includes a morphology decision engine for deriving a morphology assessment from the morphological features, a kinetics decision engine for deriving a kinetics assessment from the kinetics characteristics, and a spectroscopic analysis decision engine for deriving a spectroscopic assessment from the biochemical characteristics. The consolidation decision engine correlates and incorporates the morphology assessment, the kinetics assessment and the spectroscopic assessment in its computation.

In another feature of this aspect of the invention, the system further includes an annotation module for receiving through the graphical user interface a modification to at least one of the morphological features, the kinetics characteristics and the biochemical characteristics. The modification is provided to the consolidation decision engine and the consolidation decision engine re-computes a modified diagnostic assessment upon receiving the modification.

In yet another feature of this aspect of the invention, the system further includes a patient risk profile module for retrieving patient risk profile information from a data base, and a patient history module for retrieving patient history information. The evaluation of the assessment incorporates the patient risk profile information and the patient history information.

In yet another aspect of the invention, there is provided a method of acquiring and analyzing MRS medical image data from a region in an anatomy of a patient. The method includes the steps of obtaining a plurality of medical image data of the region, identifying from the plurality of medical image data a set of data points representing a possible lesion in the region, extracting from the plurality of medical image data features associated with the possible lesion, computing an initial diagnostic assessment of the possible lesion from the features, and upon the initial diagnostic assessment satisfying a pre-selected criteria, completing the steps of acquiring the MRS medical image data from a candidate region including the possible lesion, extracting biochemical characteristics from the MRS medical image data, re-computing a consolidated assessment of the possible lesion further incorporating the biochemical characteristics in the re-computation, and providing the consolidated assessment to a user for evaluation and modification.

In yet another aspect of the invention, there is provided a system for analyzing medical image data of a region in an anatomy, the medical image data being acquired from a plurality of modalities. The system includes an image data module for receiving the medical image data, a plurality of image processing modules, a plurality of modality decision engines, a consolidation decision engine, the consolidation decision engine combining the modality assessments and computing an initial diagnostic assessment of the possible lesion from the modality assessments, and a graphical user interface for displaying at least a portion of the medical image data along with the initial diagnostic assessment for user evaluation and modification. Each of the plurality of image processing modules identifies a possible lesion in the medical image data and extracts and classifies a set of modality characteristics associated with the possible lesion. The set of modality characteristics associated with the modality is forwarded to a corresponding modality decision engine for computing a modality assessment of the possible lesion. The modality assessments computed by the modality decision engines are combined by the consolidation decision engine in its computation.

In other aspects the invention provides various combinations and subsets of the aspects described above.

BRIEF DESCRIPTION OF DRAWINGS

For the purposes of description, but not of limitation, the foregoing and other aspects of the invention are explained in greater detail with reference to the accompanying drawings, in which.

DETAILED DESCRIPTION OF EMBODIMENTS

Figure 1:
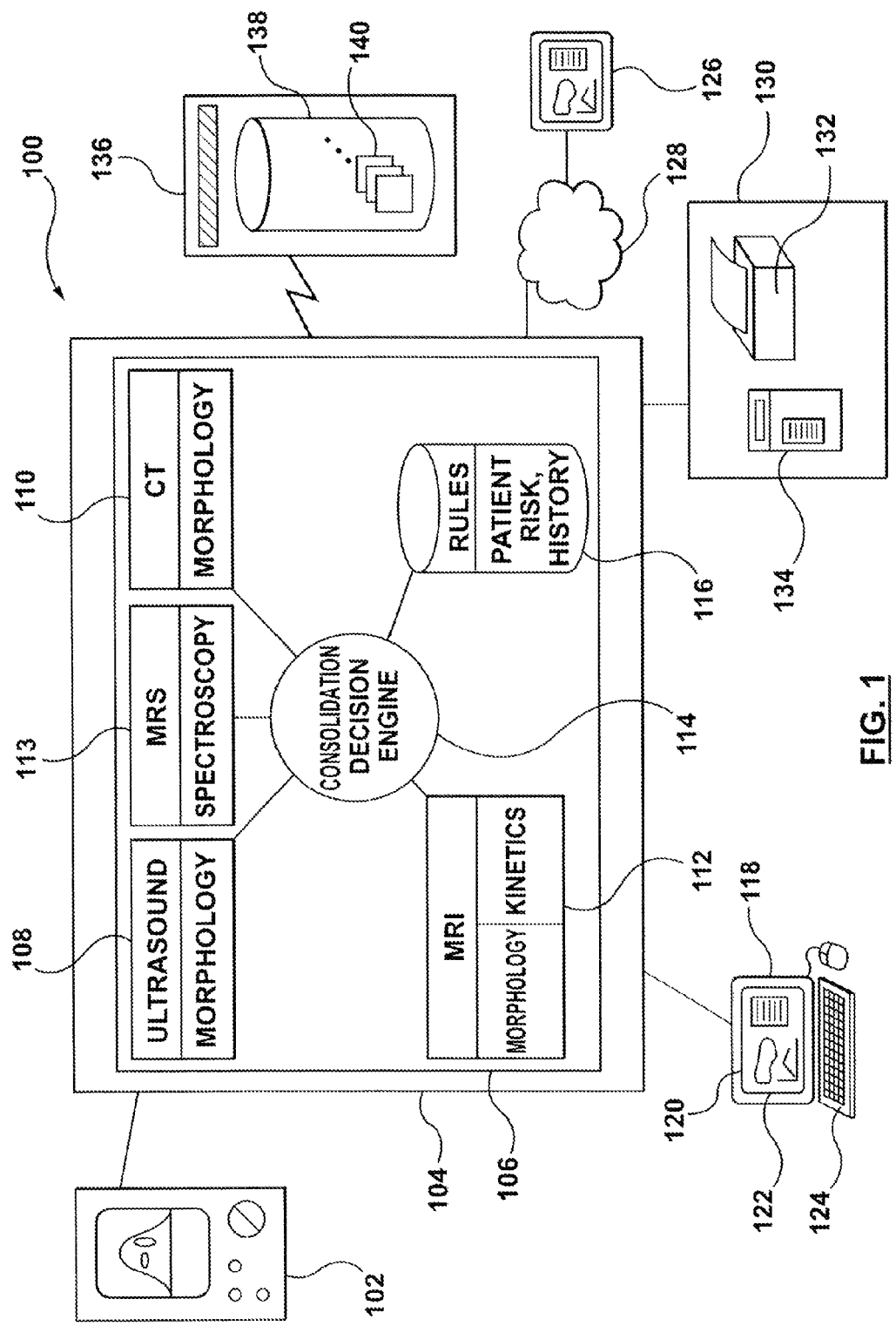
FIG. 1 is a schematic diagram showing a computer-aided detection (CAD) system.

The invention relates generally to the field of computer-aided analysis of medical images and detection of suspicious abnormalities. In particular, the invention relates to a method and system for processing medical images obtained from multiple modalities, including analysis of kinetics as well as morphological features.

The invention combines data from multiple modalities, including kinetics (quantitative), morphological (qualitative) and biochemical (quantitative) information to achieve an optimal discrimination of imaged suspicious abnormalities, such as imaged breast lesions. Morphological features of a lesion are generally those associated with size, shape, signal distribution within a mass, or border characteristics of the lesion. They include features such as whether a lesion is a mass having a round, oval or lobular shape, a mass with smooth, irregular or spiculated borders, or a mass having homogeneous, peripheral or ductal enhancement. Morphological features can be extracted from MRI, ultrasound or x-ray images, or image data from other modalities. Kinetics features relate to signal temporal behavior of imaged lesion(s) in a time sequence of images or image data. Kinetics features of MRI data generally refer to, but are not limited to, time-dependent contrast enhancement of regions in a scanned anatomy volume subsequent to administering of contrast agent. A kinetics curve may be type I (continued increase), type II (plateau) or type III (washout). Biochemical information can be obtained by analyzing MRS data, i.e., spectroscopic information, to determine the presence and relative concentration of marker chemicals (such as choline, creatine, or 31P, among others) in a single voxel or several voxels. These information are considered relevant in diagnosing cancer. A computer application program is provided for extracting morphological, kinetics and biochemical information from medical imaging data and for combining results from quantitative and qualitative analysis of the medical imaging data from multiple modalities to obtain a consolidated result.

Although a diagnostic assessment may be derived from result of any of a kinetics, a morphological or biochemical (i.e., spectroscopic) analysis of image data from a single modality, combining results from multiple modalities tends to increase the confidence level in the assessment obtained, as such consolidated assessments generally are derived from a larger data set and therefore tend to be more statistically reliable. For example, the analysis of time course kinetics can be performed before or after the evaluation of the lesions morphology in post-contrast images. Optionally, the results from the first performed analysis are evaluated prior to performing the next analysis. If results from the first performed analysis (for example, kinetics analysis) are clearly suggestive, the next analysis (for example, morphology or spectroscopic analysis) may not be necessary. On the other hand, if the results from the analysis of one mode (for example, kinetics) are indeterminate or suggest benign lesion, a further analysis (for example, morphology) may be worthwhile. Further, results from one analysis may be used as inputs to analysis of another mode. For example, results of a kinetics analysis generally include the identification of a lesion, which may be used to drive the segmentation part of the morphology process.

FIG. 1 shows a computer-aided detection (CAD) system 100. The CAD system 100 processes and analyzes images and data obtained from multiple modalities, including performing kinetics, morphological and spectroscopic analysis, for providing diagnostic assessments based on extracted kinetics, morphological and spectroscopic features. The CAD system 100 has a medical imaging device 102. The medical imaging device 102 is used by a user to acquire medical images and data by scanning or imaging a patient. Different imaging modalities may be configured for use with a CAD system 100. For example, the medical images may be ultrasound images, X-ray images, MRI images, Computed Tomography (CT) images, Positron Emission Tomography (PET) images, PET/CT, nuclear, MRS or any images or data from a suitable image or data acquisition device.

Image data acquired by the medical imaging device 102 is provided to a computer 104 for processing. Although in FIG. 1 a stand-alone computer is shown, the computer 104 may be any general purpose computer or a dedicated computer. It may also be an embedded system, such as an embedded system in an image acquisition system that includes an medical imaging device 102.

A computer program 106, namely a software application for performing the functions of a CAD system is hosted by the computer 104. The CAD application program 106 has a number of components. Corresponding to each modality, there is a dedicated component. For example, there is a ultrasound subsystem 108 that corresponds to the ultrasound modality. The ultrasound subsystem is dedicated to retrieving, processing and analyzing ultrasound image data. Similarly, there is a CT subsystem 110 dedicated to processing and analyzing CT image data. Corresponding to MRI image data, there is an MRI subsystem 112. Corresponding to MRS spectroscopic data, there is an MRS subsystem 113.

The CAD application program 106 has a consolidation decision engine 114. The consolidation decision engine 114 receives as its inputs the results from these modalities, namely from the ultrasound subsystem 108, the CT subsystem 110, the MRI subsystem 112, and the MRS subsystem 113, and computes a consolidation assessment, incorporating the results from each of these modalities. The CAD application program 106 may use rules built into the application program or stored in a database 116 for making the consolidated decision. These rules may be derived from sample images containing benign and malignant lesions or established from statistical models, or established by employing any suitable methodology.

A workstation 118 is provided. The workstation 118 provides a user interface 120 that allows a user of the system 100 to view medical images, to manipulate the images and to interact with the system to process the images. The user interface 120 includes a display 122. The display may be a display screen, or an image protector, or any other suitable display devices capable of visually presenting medical images to a user and presenting graphical and textual contents to user.

The workstation 118 displays image data and results generated by the CAD application program 106 to a user to facilitate diagnosis of the images by the user. For example, images from each modalities as well as features extracted from these images may be displayed to the user. They may be displayed side-by-side on the same display to make it more convenient for the user to make a diagnosis. Lesions identified in these medial images as well as features extracted may also be highlighted. In addition, a form conforming to medical standards may be pre-populated, incorporating any results that are automatically detected by the system. The preliminary assessment automatically computed by the system may also be shown to the user for the user to confirm or modify.

The user interface 120 also includes input devices 124 for the user to interact with the system and to identify to the system particular regions of interest in the displayed medical image. The input devices 124 may include a keyboard, for example, for the user to enter any textual input. A voice recognition module may be provided for voice-to-text transcription to allow a user to enter textual descriptions of imaged object verbally, to enter other textual inputs without having to type the text, or to issue any computer program command. It may also include a mouse or some other pointing device for the user to identify a particular pixel or region of the medical image to the system. Display 122 and input devices 124 may be physically combined into a single piece of hardware unit, such as a touch screen that is capable of both displaying graphic and textual output and receiving user input. The user interface 120 may also include a remote user interface, such as a remote terminal or a web browser 126, for sharing results with other radiologists or physicians over a telecommunication network 128. The telecommunication network 128 may be that implemented with direct cable connection, a local area network (LAN) or the Internet. The remote user interface allows a physician to remotely review images obtained by an operator from a patient and make any modification in real-time to results automatically produced by the system 100. A physician, whether in a room next door to the medical imaging device 102 or workstation 118, or in a facility a few thousand kilometers away, can make diagnosis through the remote user interface.

The system 100 also includes a number of output peripherals 130 so that a user may reproduce or record results of an analysis session or other output of the system. For example, the output peripherals may include a printer 132, either film based or paper based. A film-based printer may be used to transfer the medical images, either the original image or the processed image to a film for use with more traditional display devices that require a filmed image. A paper-based printer may also be used to produce hard copy reports for sharing with other physicians or for archiving purposes. In addition, the output peripherals 130 may include DICOM-compliant devices 134 for transferring or storing processed results, namely composite images generated by the system together with associated reports.

The system 100 has access to an image archive server 136. The image archive server 136 may be part of the system 100. It may also be provided by an external service provider, such as a hospital information system. The image archive server 136 has a server database 138 for storing archived images 140. When the CAD application program 106 requests archived images 140 from the image archive server 136, the image archive server 136 retrieves the requested image from the server database 138 and sends the requested images to the CAD application program 106. As will be understood, the archived images are all images already acquired by a medical imaging device. The archived images can be images from any supported modalities, such as MRI, CT, or PET. The archived image data can also be images combined from different modalities, such as digital tomosynthesis image data. The archived images 140 are not necessarily of the same modality as the medical imaging device 102 that is currently directly connected to the computer 104. For example, the computer may be connected to an ultrasound imaging device, while the image archive server 136 may contain images acquired previously from a CT imaging device or an MRI imaging device. Further, although in FIG. 1 there is shown only one image archive server 136, it will be understood that there may be several image archive servers connected to the computer 104. In addition, each image archive server 136 may not necessarily have only one database, it may have access to a number of databases, and these databases may be physically located at different sites.

System related or generated data are generally stored together with the archived images 140. For example, the archived images may be stored along with annotations made on the image by a physician during a previous analysis or diagnosis data. Preferably, the image archive server 136 supports archiving DICOM-compliant images, as well as images of other formats such as JPEG, BITMAP, among others. Annotations, comments, results of image processing all can be archived as part of a DICOM-compliant file. Audit information, such as user ID, date or time stamp of processed images, and user addition or modification of detected features all can be recorded for each archived instance of a processed image, as well.

Figure 2:
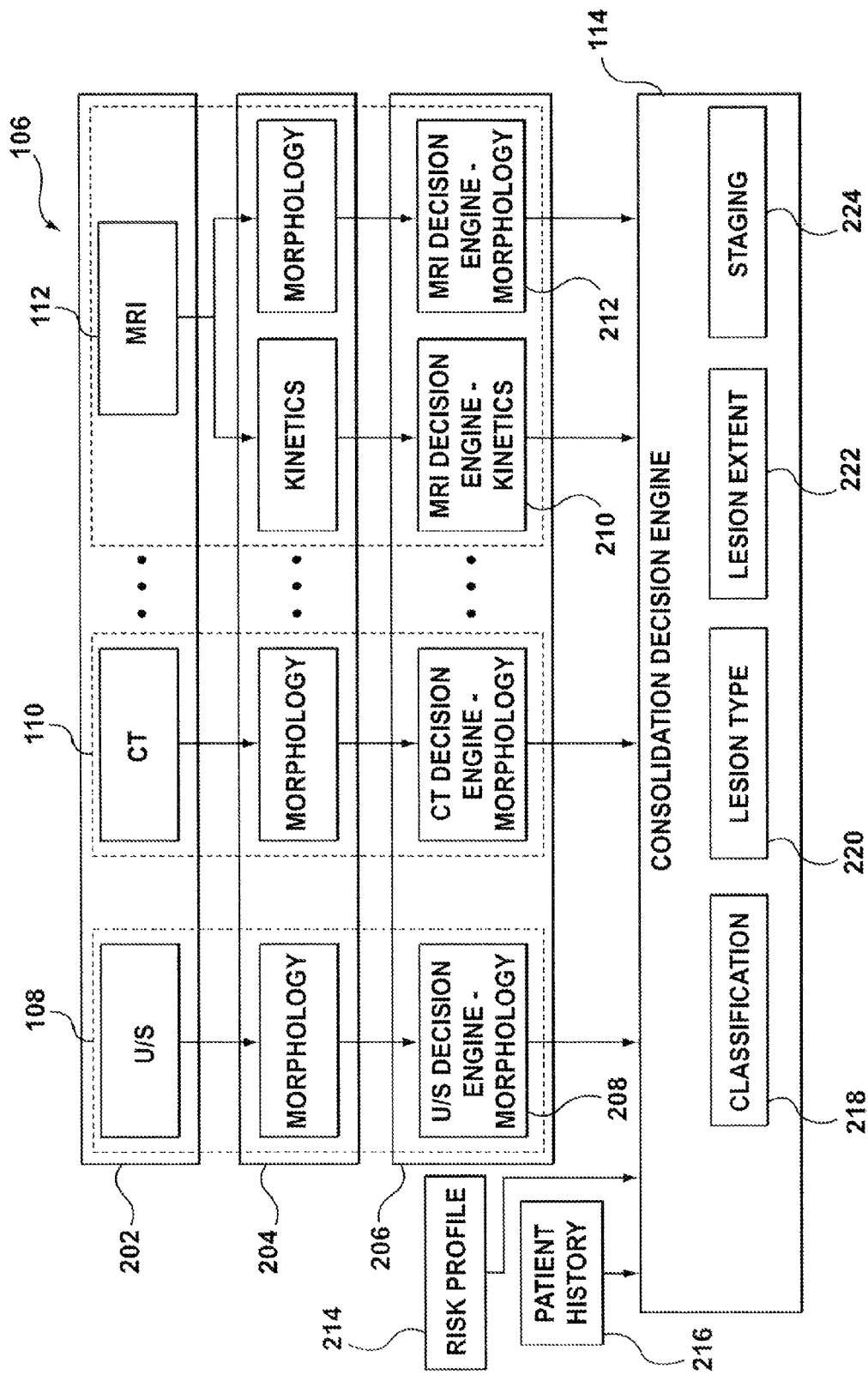
FIG. 2 is a block diagram of major functional components of a CAD application program of the CAD system shown in FIG. 1.

FIG. 2 is a block diagram of major functional components of the CAD application program 106 of one embodiment. As shown in FIG. 2, the CAD application program 106 has an image data module 202, a processing module 204 and a modality decision engine 206, for retrieving and analyzing image data. As will be described in detail below, the image data module 202 retrieves image data from medical imaging device 102 or image archive server 136 and pre-processes the image data to extract images or other data from the image data for further processing. Images retrieved and pre-processed by the image data module 202 are forwarded to the processing module 204. The processing module 204 is provided for extracting information that are relevant to diagnosing disease from the pre-processed image data. For example, this module may be provided for identifying suspected lesions in an image and extracting from the image those features associated with the suspected lesions that are considered relevant to diagnosing disease, i.e., discriminating the lesions. The modality decision engine 206 classifies a lesion based on the information extracted and computes an assessment of the lesion from the extracted information. Such assessment can be computed, for example, based on a pre-established set of rules or using a pre-selected algorithm.

The CAD application program 106 is modular in that each of image data module 202, processing module 204 and modality decision engine 206 has a component for a supported modality. For example, the modality decision engine 206 has as its ultrasound component an ultrasound decision engine 208, its MRS component an MRS decision engine (not shown), and its MRI component an MRI morphology decision engine 210 and an MRI kinetics decision engine 212. As an image or scan data obtained from a particular modality is processed by the CAD application program 106, the image or scan data is processed by the corresponding modality components of image data module 202, processing module 204 and modality decision engine 206. Components of image data module 202, processing module 204 and modality decision engine 206 of a particular modality form the subsystem of that modality. For example, ultrasound components of image data module 202, processing module 204 and modality decision engine 206 form the ultrasound subsystem 108. To handle images or data of another modality, a corresponding component is added to each of image data module 202, processing module 204 and modality decision engine 206, without having to change the overall architecture of the CAD application program 106. Each modality requires its own component because, in general, image data obtained from one modality typically have certain unique aspects not found in other modalities. For example, certain sonographic characteristics associated with ultrasound images, such as echo patterns, generally are not exhibited in x-ray images. Similarly, spectroscopic processing is generally unique to the MRS modality.

FIG. 2 shows that MRI modality has two components in each process module 204 and modality decision engine 206, one for processing and extracting morphological characteristics associated with a lesion imaged in an MRI scan, and another component for processing and extracting kinetics, namely, temporal, characteristics associated with a time sequence of MRI scans.

The CAD application program 106 has a consolidation decision engine 114. The consolidation decision engine 114 combines all results obtained from each modality, together with patient data, to compute a consolidated score for lesions identified by individual modalities. The patient data may include, for example, risk profile of a patient or the patient's history or both. A risk profile module 214 is provided. The risk profile module 214 extracts risk profile information from a database 116, processes the risk profile information and provides the results to the consolidation decision engine 114. Risk profile information may include presence of specific genes—e.g., breast cancer susceptibility gene (also known as BRCA-1). A patient history module 216 is also provided. The patient history module 216 extracts information pertinent to a patient's history, processes the history information and provides the processed history information to the consolidation decision engine 114. Patient history may include familial history of breast cancer, previous diagnosis and treatments of cancer. Patient history information may also include information relating to images of the same lesion taken during previous clinic sessions, for example, a few months ago. The patient history module 216 can use the information about images taken previously and direct the image data module 202 to retrieve these previously taken images for comparison with images currently processed.

The consolidation decision engine 114 has several individual components. These individual components include a classification module 218, a lesion-type module 220, a lesion-extent module 222, and a staging assessment module 224. The same lesion generally can be seen in multiple modalities. Each of the modules 218, 220, 222, 224 may include components for processing the image data from each modality. A composite image can be generated and displayed to show results from multiple modalities. For example, results of MRS modality can be overlaid onto an image of one of the image modalities and shown together with the image. The consolidation decision engine 114 correlates results of analysing the lesion seen in images, including biochemical information on chemical composition of the tumor obtained through a multivoxel or single voxel MRS analysis, from multiple modalities to produce a consolidated result.

For example, in one implementation, the classification module 218 combines results from all modalities to provide a possible classification of the lesion. For example, local morphological characteristics, such as local spiculation, local branch pattern, local duct extension, detected by all modalities can be combined and compared against a set of pre-defined feature list to classify the lesion as belonging to ACR BI-RADS® 5 category or an ACR BI-RADS® 4a category. Similarly, the lesion-type module 220 combines results from all modalities to derive a possible type of a lesion, such as DCIS or CA. The lesion-extent module 222 combines results from all modalities to arrive at an estimated size and outline geometric contour of the lesion. The staging assessment module 224 combines as inputs the results from all modalities and the consolidated classification, type and extent, together with the patient's risk profile and the patient's history information, to compute or produce a suggested assessment of lesion stage. The consolidated result, which includes classification, type, and extent of a lesion as well as suggested diagnostic assessment of lesion stage, is shown to the user through the user interface 120.

It will be understood other implementations are also possible. For example, one may have one ultrasound subsystem for processing ultrasound images. Namely, one may have a classification module, a lesion-type module, a lesion-extent module, and a staging assessment module devoted to processing ultrasound images. One may have another MRI subsystem that have its own classification module, lesion-type module, lesion-extent module, and staging assessment module devoted to processing MRI images, or other subsystems for other modalities. A consolidation engine will then combine results from each modality subsystem to produce a consolidated result. Other implementations that provide the processing of multiple modalities but combine the modules differently are also possible, as long as all necessary processing, such as classification, determination of lesion type and lesion extent etc., is provided for all modalities and a consolidated result is obtained from consolidating results from all modalities.

This consolidated result is subject to user confirmation or modification. For example, a user can modify an automatically detected feature in an image from one of the multiple modalities. It will be appreciated that any modification to features detected in one modality may affect detection result with respect to a lesion at the modality level, and may further change the consolidated result. A user may also modify directly a consolidated result automatically produced by the consolidation engine. Whatever the modification is made by the user, the modification is communicated back to processing module 204, modality decision engine 206, or the consolidation decision engine 114, as the case may be. A modified consolidated result, including a modified suggested assessment of a lesion stage, is re-calculated and presented to the user again for modification or confirmation. Once confirmed, a report can be automatically generated, summarizing the results of the analysis and assessment of these medical images.

Figure 3:
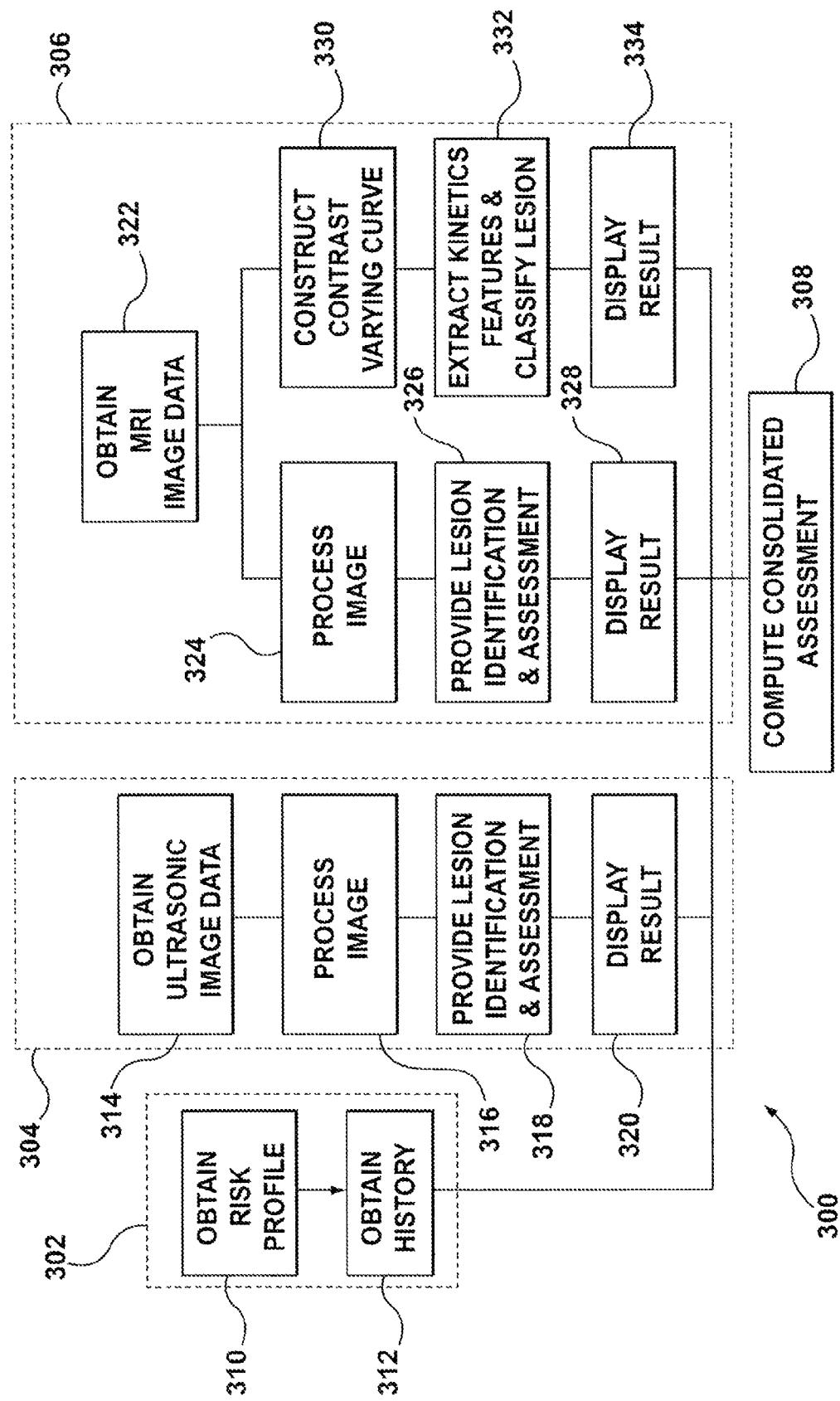
FIG. 3 is a flowchart showing steps of a process for analyzing medical image data quantitatively and qualitatively implemented by the CAD application program shown in FIG. 2.

In operation, a user directs the CAD application program 106 to retrieve medial images or data generated by an imaging acquisition device or to retrieve previously scanned and archived images or data from image archive server 136 for processing and analysis. The user may issue the direction from the user interface 120 provided by the workstation 118, for example, or a remote user interface such as a web browser 126. FIG. 3 shows in flowchart format a process 300 followed by the CAD application program 106 to analyze and process images contained in the image data and generate a consolidated assessment.

FIG. 3 shows three parallel sub-processes, namely, a patient profile data retrieval sub-process 302, an ultrasound sub-process 304, and an MRI sub-process 306. The sub-processes are shown as parallel processes. These sub-processes are not necessarily executed parallel in time but rather, they are independent of each other. These sub-processes can be performed in any time sequence relative to each other, provided that the results of the sub-processes are all available prior to the final step, computing consolidated assessment (step 308). For example, patient data related to patient risk profile or history may be retrieved before, after, or during the process of ultrasound images. However, as will be appreciated, in an actual implementation of the process 300, results from one modality often can serve as inputs (or at least part of the inputs) to another modality. For example, if the MRI sub-process 306 is first applied to a set of MRI data, a lesion centroid can be identified in an analysis of signal enhancement in concentrated areas or a volume. The lesion centroid so identified can serve as the starting point of a segmentation process for the MRI morphology process. Although sub-processes corresponding to two modalities are shown, sub-processes corresponding to other modalities, such as CT modality, can be added. As these other modalities follow steps similar to that of the ultrasound modality or MRI modality, they are not shown in FIG. 3.

Referring to FIG. 3, each of these three sub-process is now described. Patient data retrieval sub-process 302 starts with the risk profile module 214 retrieving risk profile data of the patient from a database 116 (step 310). The database may be directly accessible to the CAD application program 106 as shown in FIG. 1, or it may be necessary to request the information from a database maintained externally, such as by a hospital information system. Next, at step 312, the patient history module retrieve patient history information, from the database 116 where the patient's risk profile data is maintained or from some other externally maintained database. The risk profile information and the patient history information are forwarded to the consolidation decision engine 114 for its use at step 308, to compute a consolidated assessment, as will be described below.

The ultrasound sub-process 304 starts with obtaining ultrasound image data, step 314. The ultrasound image data may be obtained from the medical imaging device 102. Alternatively, the CAD application program 106, namely its image data module 202, may request the ultrasound image data from the image archive server 136. Generally, the obtained ultrasound image data contains information in addition to medical images. At this step, individual images are also extracted from the image data. An extracted image is forwarded to the processing module 204 for image processing.

At step 316, the ultrasound component of the processing module 204 processes the image. At this step, the processing module 204 computes, i.e., extracts and identifies, physical, texture, morphological as well as sonographic characteristics associated with an object of interest in the separated individual images. The object of interest may be defined by the boundary of an abnormal region such as a lesion. At step 318, the ultrasound decision engine 208 analyzes these characteristics to provide classification, lesion type identification, and lesion assessment. Optionally, features extracted and identified are shown to a user for confirmation or modification, at a display and confirmation step 320.

Figure 4:
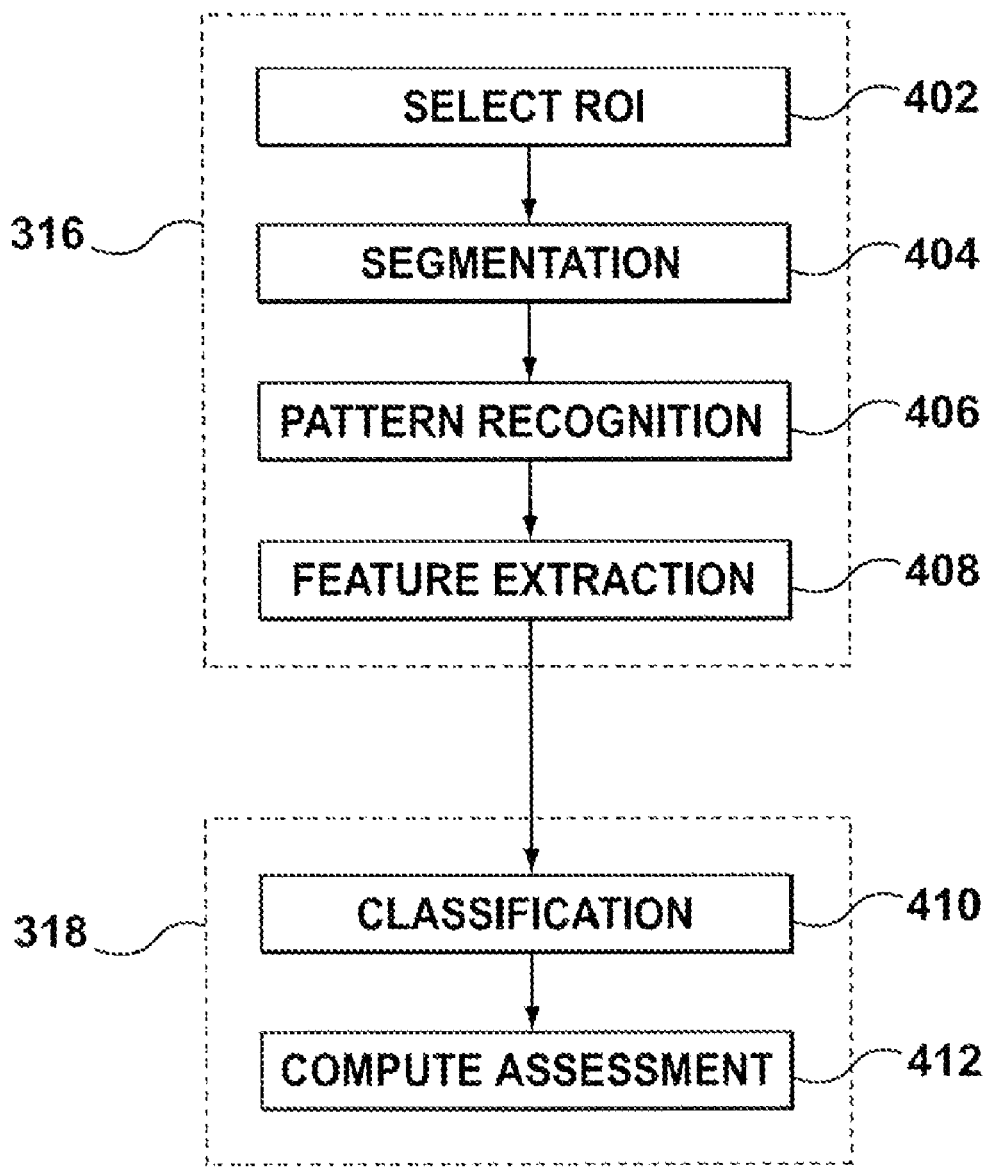
FIG. 4 shows in detail a portion of the process shown in FIG. 3.

FIG. 4 shows in detail the sub-steps by the CAD application program 106 when processing morphological features in an ultrasound image. The ultrasound image can be a 2-dimensional image of an area or a 3-dimensional image of a volume. The image processing step 316 starts from a step of selecting a region of interest ("ROI"), step 402. An ROI is a region in an anatomy that may contain an abnormal object such as a lesion. An ROI can be 2-dimensional, when a 2-dimensional image is processed, or 3-dimensional (also called "VOI", or "volume of interest"), when an imaged volume is processed.

An ROI may be identified in any suitable manner. For example, a user can manually identify an ROI on a displayed image through the user interface 120. The CAD application program 106 can extract an ROI already identified from another source, such as an ROI identified on a prior exam and now stored in a database. Or, the CAD application program 106 can perform a morphological analysis of the image to identify an ROI and suggest it to a user. In one implementation, the user selects and identifies the ROI to the system by first selecting a segmentation "seed point", i.e., a starting point in the interested region. The user may select the segmentation seed point by, for example, using a pointing device and selecting the point in the central region of a suspected lesion. The ROI is then defined by dragging the cursor away from the seed point so that a circle is formed around the seed point. The circle constrains the region into which the segmentation algorithm operates. The user releases the pointing device when the ROI is sufficiently large so as to enclose the entire suspected lesion.

Once the ROI is identified, the ROI is segmented at a segmentation step 404 to delineate the boundary of the suspected lesion. After an ROI is segmented, a pattern recognition operation (step 406) is applied to the segmented ROI to identify and extract morphological characteristics from the ROI. During the pattern recognition step 406, structural characteristics in the ROI are identified and analyzed. They are classified based on their morphological and texture patterns or features. Local morphological characteristics such as local spiculation, local branch pattern, local duct extension and local micro-lobulation are identified and indexed. In addition, pixels in the ROI are scanned to identify sonographic characteristics such as echoing patterns. The local morphological characteristics are combined with a set of sonographic characteristics, pre-defined by a standard such as ACR-BIRADS lexicon, to generate a list of features so identified. At the pattern recognition step, processing module 204 may also analyze the image to identify features such as clustering and contrast of pixels in the segmented ROI or analyze the image to incorporate some notion of the domain knowledge such as information of pixels surrounding the ROI in order to better identify specific local features.

Next, at a step of feature extraction (step 408), the processing module 204 extracts from these locally identified patterns certain special features that are considered relevant to diagnosing cancer, i.e., discriminating between benign and malignant lesions. Some of these features may include shape, orientation, angular margin, lesion boundary and calcification. The features may also include those unique to a specific detection technology. For example, for an ultrasonic image, the features may include echo patterns and posterior acoustic features.

Next, at a classification step 410, the features and characteristics extracted and identified during the image process step 316 (sub-steps 402 to 408) are combined and analyzed. Conveniently, the features or characteristics extracted and identified generally coincide with a pre-defined set of characteristics. Pre-defined sets of characteristics and features are generally developed by the medical profession as being relevant to diagnosing disease, such as cancer. Descriptions of these features are generally provided together with a definition of these features. One such set of pre-defined characteristics and lexicon is the BI-RADS lexicon. At this step, the features extracted and identified are compared against the set of the BI-RADS lexicon to assign a statistical likelihood that any feature in the set may present in the lesion being analyzed.

Next at step 412, an assessment of the lesion is computed. Rules or algorithms can be developed for computing an assessment. The assessment can be computed from, for example, the classification and the likelihood of features identified and classified according to BI-RADS lexicon. In one implementation, a large collection of medical images is first processed. Pattern recognition and feature extraction operations are applied to each image in the collection. Features identified are classified and indexed according to the scheme and lexicon defined by BI-RADS. Images in the collection are also diagnosed, based on, for example, biopsy results. From the results of image processing and known diagnosis, a statistical model linking the set of features extracted and a statistical likelihood of a diagnosis can be developed. A set of rules for computing an assessment can be extracted from the model, which can then be applied to the results of an analyzed image to produce an assessment. It will be appreciated that the computation of an assessment is not limited to using a statistical model. The assessment may also be computed using a super vector machine (SVM) method or may be generated using an AI engine that employs a more complicated approach such as a neural network method. Whatever the method used, an assessment is computed at this step from the features identified, extracted and classified.

Methods and systems directed to extracting morphology features from a medical image and providing a suggested assessment of suspicious lesion based on morphology features extracted and classified are also described with further detail in co-pending, co-owned U.S. application Ser. No. 60/686,397, filed on Jun. 2, 2005, which application are incorporated by reference herein in its entirety.

Returning to FIG. 3, the steps of the MRI sub-process 306 are now described in detail. As shown in FIG. 3, the MRI sub-process 306 starts at a step 322 of obtaining MRI image data. The MRI image data may be supplied by the MRI medical imaging device 102, or may be retrieved from image archive server 136. In one implementation, the MRI image data are acquired in multiple MRI scans, forming a time sequence of MRI image data. From these series of MRI scans, temporal information associated with suspicious abnormalities, such as suspected lesions, can be extracted in a kinetics analysis.

In general, a medical image is formed by a medical imaging device by differentiating between specific types of tissues. Increasing the contrast between the types of tissues tends to provide better image quality. Administering contrast enhancement agent to a patient may selectively affect imaging properties of certain tissue types and enhance contrast between normal and tumor tissues and therefore contrast of imaged lesions. Gadolinium based contrast agent (e.g., Gd-DTPA) is one such commonly used contrast enhancement agent for MRI images. Typically, a benign or a malignant lesion will exhibit different temporal contrast-enhancing behavior subsequent to the administering of a contrast agent. A series of MRI scans, performed at regular time intervals, such as every two minutes, can be performed on a patient after injection of contrast enhancement agent to capture temporal contrast-enhancing behavior. The series of MRI scans therefore contain a time sequence of MRI data. One diagnosing technique is to analyze a contrast variation curve constructed from the time sequence of MRI data. Various kinetics features relating to a model or diagnosing methodology are extracted from the contrast variation curve for further analysis.

Figure 5:
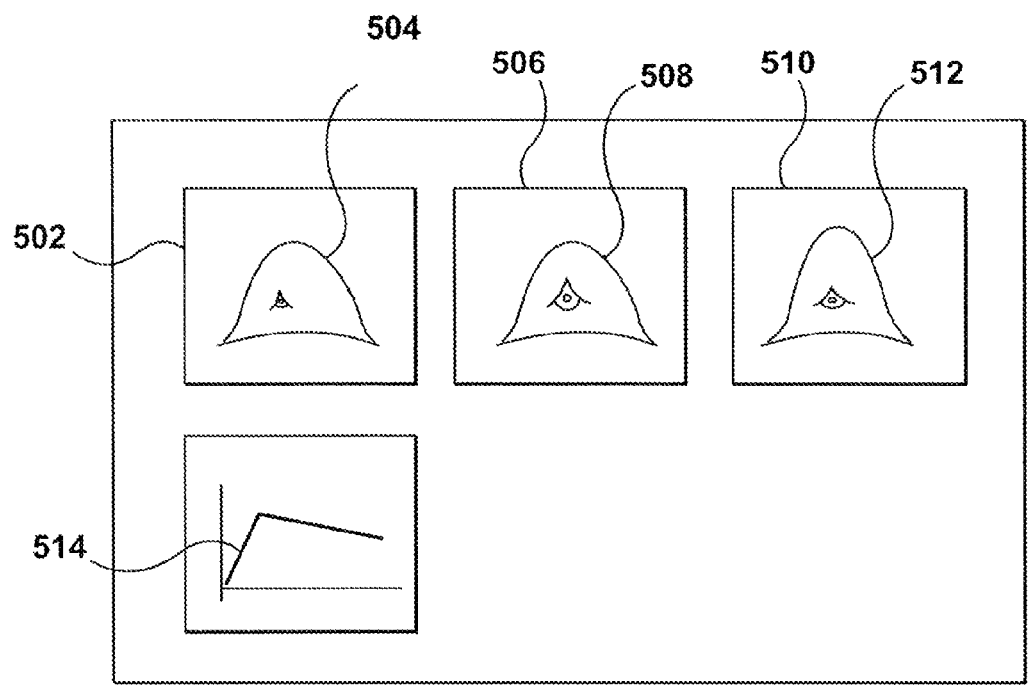
FIG. 5 illustrates schematically a time sequence of medical images and a corresponding contrast variation curve.

FIG. 5 illustrates schematically one such time sequence. Only three images in such a time sequence are shown schematically in FIG. 5 although more typically will be used. The first window 502 illustrates a pre-contrast scan image 504. It shows a lesion imaged prior to the contrast enhancement. The lesion shows visible structures but not any detail nor its true extent. The second window 506 shows a contrast enhanced image 508. The image, because of enhanced contrast, shows in greater detail the imaged lesion. It also shows the actual extent of the lesion, thanks to an enhanced contrast between the tissues of the lesion and its surrounding normal tissues. The third window 510 illustrates schematically a time delayed image 512. The lesion, due to the residual contrast enhancement effect, is still more visible than that in the pre-contrast scan image 504; however it is less visible and shows less detail than that in the contrast enhanced image 508.

Also illustrated in FIG. 5 is a window showing a contrast variation curve 514. The contrast variation curve 514 is a curve showing the contrast variation in time subsequent to the administering of a contrast agent. The curve generally shows an initial increase of the contrast followed by a decline of the contrast enhancement as seen in the MRI images 504, 508, 512 in the time sequence.

It is believed that in general the time variation characteristics, namely kinetics of MRI image data and in particular, the characteristics of the contrast variation curve, can be an useful aid in diagnosing cancer. Relevant kinetics features generally are those global or local criteria that can be derived from contrast variation curves and considered important descriptors for or by a statistical model. One such kinetics feature is simply the shape of a contrast variation curve. A display similar to that shown in FIG. 5 may be presented to a user. The CAD application program 106 may analyze the contrast variation curve 514 and provide an assessment of the imaged object, namely the suspected lesion, to assist the user in making a diagnosis.

Figure 6:
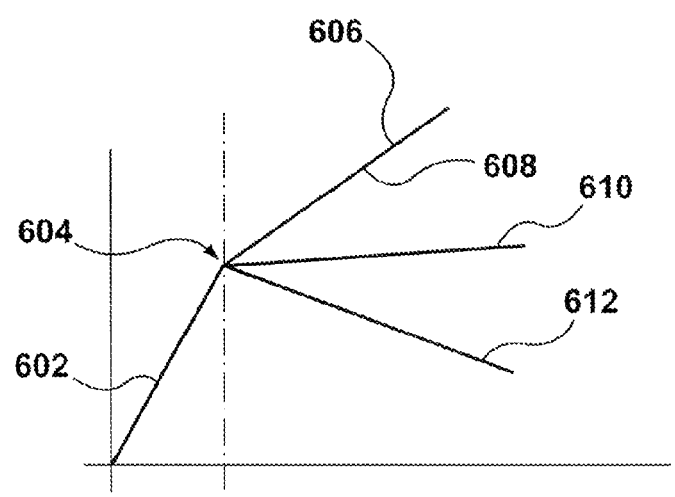
FIG. 6 shows general behaviours that can be expected of a contrast variation curve.

FIG. 6 shows the general behaviours that can be expected of a contrast variation curve. A contrast variation curve generally consists of an uptake segment 602, a transition point 604, and a time delayed portion 606. Advantageously, the contrast variation curve shown in FIG. 6 is normalized, namely shows only the relative enhancement of contrast. A normalized curve shows the rate of increase (and decrease) of percentage of contrast enhancement. This tends to reduce the variation from patient to patient.

The initial enhancement of contrast induced by the contrast enhancement agent is shown as an initial rapid increase of contrast, or a steep uptake segment 602. The steeper the curve, the more rapid the enhancement is. This initial increase is generally associated with the increased level of contrast agent within vasculature associated with a lesion. After the initial rapid increase of contrast, the rate of increase slows down and generally exhibits one of three different types of behaviors, depending on the type of the lesion. The transition point 604 on the contrast variation curve marks this slowdown. The first type is a slower but continued increase of contrast enhancement. The continuous enhancement 608 is generally considered indicative of a benign lesion. The second type is persistent enhancement, or a plateau 610. The contrast, after an initial rapid increase, abruptly stops increasing and maintains a roughly constant elevation of contrast in the intermediate and late post-contrast periods. A third type is a slow decline showing a wash-out segment 612. The transition point 604 corresponds to a peak enhancement. The contrast, after an initial rapid increase, abruptly stops increasing and starts declining in the intermediate and late post-contrast periods, producing the wash-out segment 612. The presence of either the plateau 610 or the wash-out segment 612 is believed to be indicative of tumor angiogenesis and vascular permeability. It is generally believed that the growth and metastatic potential of tumors can be directly linked to the extent of surrounding angiogenesis. Analyzing the contrast variation curve 514 may therefore provide an additional indicator to discriminate between benign and malignant lesions.

The MRI sub-process 306 bifurcates into two branches after step 322 at which individual image data of MRI scans are extracted. One branch is similar to processing morphological features in individual ultrasound images as described in connection with FIG. 4, which has the steps of processing image (step 324), analyzing and assessing lesion (step 326) and optionally displaying results to a user for confirmation and modification (step 328). These steps are generally the same as that described in connection with the ultrasound sub-process 304 and will not be described in further detail here.

However, it will be noted that, as MRI data may contain a time sequence of multiple scans, the step of processing image (step 324) can incorporate the temporal information in a morphological analysis. To illustrate this, consider a pre-contrast scan and a post-contrast scan. Subtracting voxel values in the pre-contrast scan from the corresponding voxel values in the post-contrast scan tends to emphasize regions in the scanned volume that are enhanced, i.e., regions that may correspond to structures in a suspicious lesion. As will be appreciated, mathematical operations other than subtraction can be performed. Further, a series of mathematical or logical operations may be applied to (or between, if logical operations) several, including multiple post-contrast, scans where appropriate, in order to assist the morphological analysis.

The other branch of the MRI sub-process 306 includes the steps of extracting and processing kinetics data (step 330), classifying lesion and computing an assessment based on kinetics features extracted (step 332), and optionally displaying results to a user for confirmation and modification (step 334). These steps are described in great detail below in reference to FIGS. 5 to 8.

MRI image data generally corresponds to a three-dimensional region or volume, represented by data points (or "voxels") arranged in a 3-dimensional grid or lattice. The 3-D volume represented by the MRI scan can be processed as a unitary volume in a 3-D processing. Alternatively, such a 3-dimensional scan can be organized into a stack of planar "slices". A user can choose to process the stack slice by slice in a series of 2-D processes.

Figure 7:
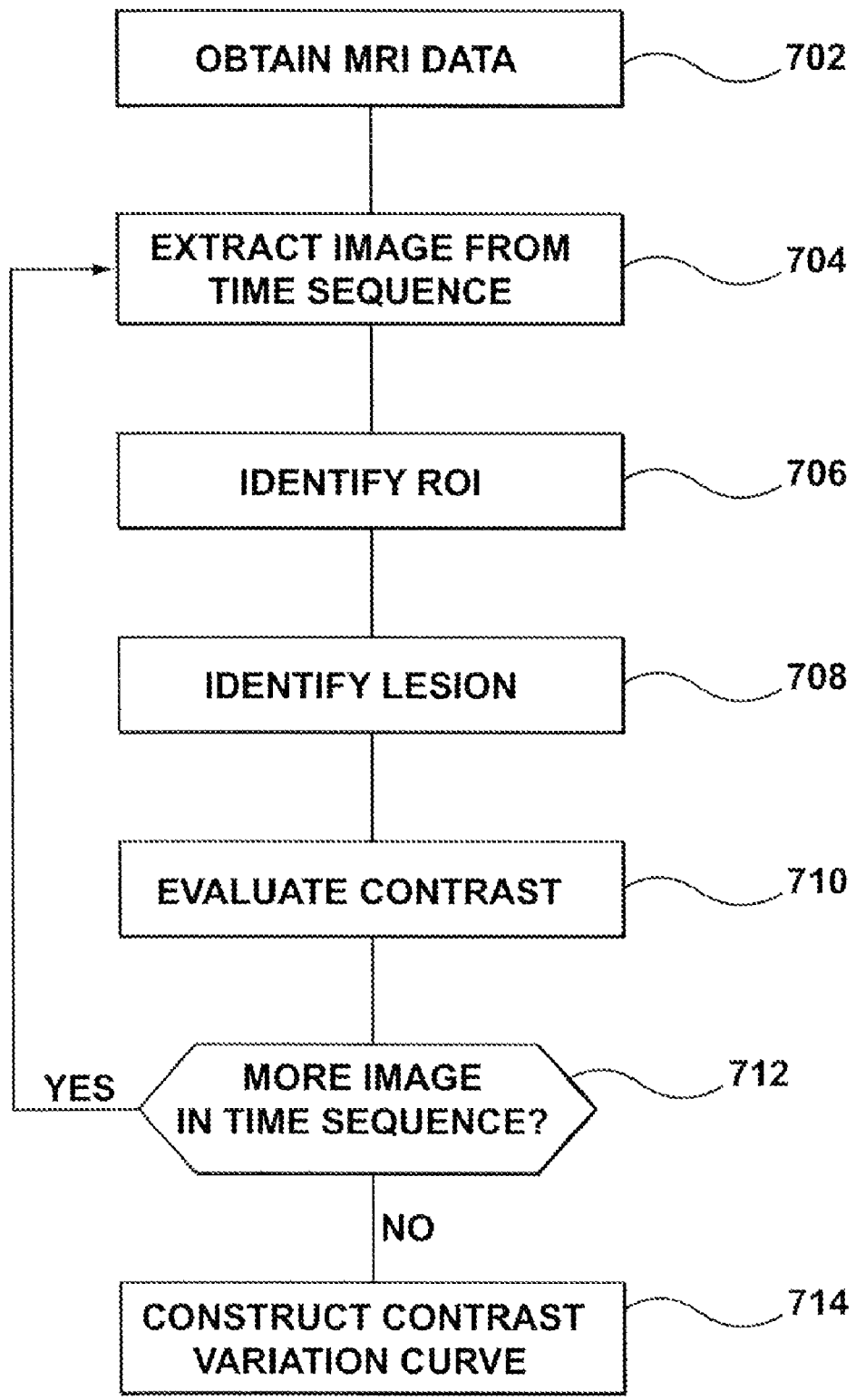
FIG. 7 is a flowchart showing a portion of the process shown in FIG. 3 for constructing a contrast variation curve shown in FIGS. 5 and 6.

FIG. 7 is a flowchart showing in detail the kinetics branch of the MRI sub-process 306 for constructing a contrast variation curve. These steps correspond to steps 322 and 330 shown in FIG. 3. The first step, step 702, is to obtain MRI data from either the medical imaging device 102 or from an image archive server 136. Image data acquired from a scan at a first initial time, prior to the administering of contrast-enhancement agent, are first extracted (step 704).

Advantageously, results from the morphological branch of the MRI sub-process 306 or morphological analysis of the ultrasound sub-process 304 can be re-used here. The same lesion identified during the morphological analysis can be selected for the kinetics analysis (step 706). If no morphological analysis has been performed and no ROI has been identified for the MRI scan, an ROI can be identified manually by a user or from the time sequence. For example, the time sequence of MRI scans can be processed to identify voxels that have marked increase of signal strength over the time course. The time delayed behavior (e.g., plateau or washout) can be analyzed as well. Voxels showing enhanced contrast and exhibiting expected time delay behavior are likely within a centroid corresponding to a lesion. An ROI enclosing these voxels may be selected automatically. The clustering of such voxels can be analyzed to isolate one lesion from another, or to group different structural elements belonging to the same lesion together. An ROI can be defined that enclose all voxels potentially belonging to a lesion.

Next, at step 708, morphological operations, including segmentation and pattern recognition, are applied to the ROI to delineate a centroid containing the lesion and to identify structures in the lesion. Again, results produced by the morphological branch of the MRI sub-process can be re-used here. Further, as will be described below, if the ROI is identified from an analysis of time-dependent contrast enhancement, the clustering of voxels may already provide a good segmentation. Next, at step 710, the contrast between the identified morphological features, namely the signal strength of the lesion relative to the surrounding structure, is evaluated. In one implementation, signal strengths of all voxels within an identified centroid is summed to provide an estimate of the contrast value of the suspected lesion. However, other ways of representing contrast enhancement can be used. For example, in a model taking into account rim enhancement, total signal strength can be the sum of voxels located along the boundary of a lesion. When another diagnostic methodology or model is implemented, voxels corresponding to some other structures may be summed. In other words, the contrast value can be a sum over voxels in any specific subset in the lesion, depending on diagnostic methodology or model implemented or supported by the CAD application program.

After a contrast level of the first pre-contrast image is evaluated, the process continues with extracting the MRI data of the next scan in the time sequence. Namely, the process returns to the image extraction step, step 704. Subsequent to the image extraction step, the steps 706 to 710 are repeated for the first post-contrast scan. First, the same lesion already identified is re-used here to provide a starting point in ROI identification. An ROI enclosing these voxels may be re-used as well. Following the identification of ROI at step 706, morphological operations are performed to identify and delineate a centroid containing the lesion at step 708. Next, the contrast between the lesion and its surrounding tissues in this first post-contrast scan is computed at step 710. These steps are repeated for all MRI scans in the time sequence until all MRI scans in the time sequence have been processed (step 712). At a final step 714, contrast values of the lesion computed from the series of images are normalized against the initial contrast value and a contrast variation curve 514 is constructed.

Returning to FIG. 3, once a contrast variation curve is constructed, a quantitative analysis of the contrast variation curve 514 is performed to extract temporal, i.e., kinetics features from the time sequence of images to provide a classification of the lesion (step 332). A quantitative analysis of the contrast variation curve 514 generally includes an analysis and classification of the shape of the kinetics curve, namely whether the time delayed portion 606 is a continuous enhancement 608, a plateau 610, or a wash-out segment 612, the level of enhancement at the transition point 604, the time to reach the transition point 604, i.e., the slope or the initial rate of increase of the uptake segment 602, and the rate of decline in the post-contrast period, i.e., the presence or absence of a wash-out segment 612 and its rate of decline. The underlying lesion can be classified based on these kinetics features. In one implementation, a lesion is simply assigned a score of 0 if a continuous enhancement is seen, a score of 1 if a plateau is seen, and a score of 2 if a wash-out segment is seen, where 0 indicates a benign lesion and 2 indicates a malignant lesion. More sophisticated classification schemes can be implemented by taking into account of other features, such as the slope of the uptake segment, the peak value of the curve, or the rate of decline. Such a sophisticated scheme generally may be established using a statistical model, similar to that described earlier in connection with ultrasound images.

Referring to FIG. 3, as a final step, results from each of these parallel sub-processes are forwarded to the consolidation decision engine 114 for making a consolidated assessment (step 308). The consolidation decision engine 114 correlates the features identified and extracted for the lesion from all modalities. Results from all modalities are also combined to provide a consolidated estimate of the extent of the lesion, to classify the lesion and to stage the lesion, namely to provide a stage assessment of the lesion according to a pre-defined staging scheme.

Figure 3A:
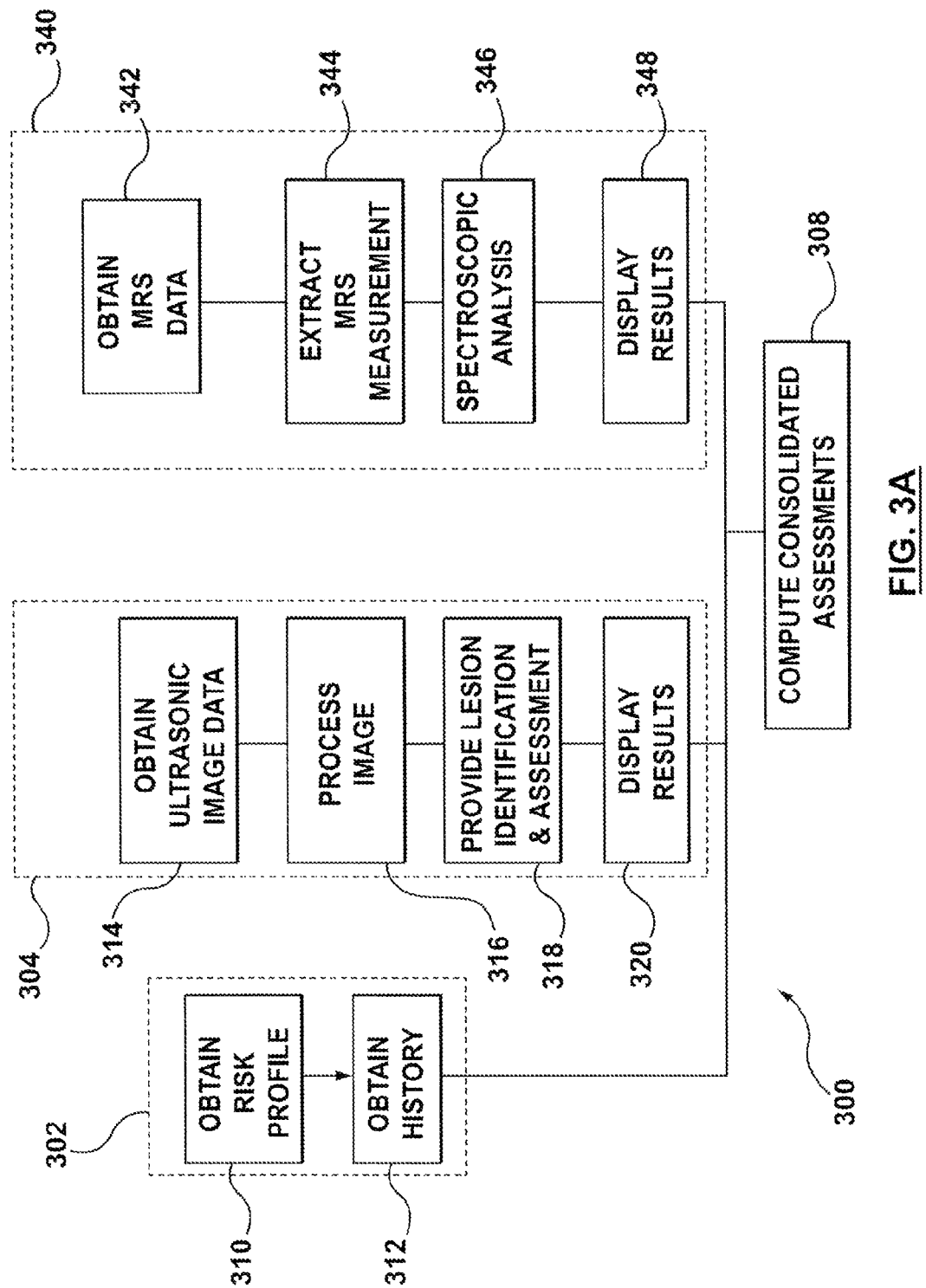
FIG. 3A shows another process for analyzing MRS data and ultrasound images, implemented by the CAD application program.

As described earlier, the CAD application program 106 is modular. Although FIG. 3 shows a flowchart implementing two modalities, namely a ultrasound modality and an MRI modality, other modalities, namely other sub-processes, can be easily added to the CAD application program 106. Any one of the ultrasound or MRI modalities can also be replaced or substituted with other modalities as well. For example, in FIG. 3A, there is shown an alternative embodiment that implements an MRS modality. In FIG. 3A, an MRS sub-process 340 replaces the MRI sub-process 306, while the ultrasound sub-process 304 is substantially the same as described in reference to FIG. 3 and therefore will not be further described here.

Referring to FIG. 3A, the MRS sub-process 340 starts with obtaining MRS data, step 342. As will be appreciated, the MRS data may be obtained directly from an MRS device 102, for example, a procedure performed based on results from other modalities. Alternatively, the MRS data may be retrieved from an image archive server 136.

In general, the MRS data corresponds to a number of MRS measurements. Each MRS measurement may be a single spectrum, corresponding to spectroscopic data obtained from chemicals in a single voxel. The MRS measurement may also correspond to spectroscopic data from chemicals in multiple voxels, such as data obtained from 2DCSI or 3DCSI exams. In a 2DCSI or 3DCSI exam, each measurement corresponds to spectra of chemicals from multiple voxels, each of which may be, for example, 1 cm3 to 1.5 cm3 in volume. A measurement is extracted from the MRS data at step 344 for further analysis.

At the next step, the strength or concentration of the marker chemicals is identified and computed in a spectroscopic analysis 344. For example, the spectrum of choline may be isolated or identified from the spectroscopic data. The peaks of choline characteristic frequencies are identified and measured and then converted to an absolute measure of concentration of choline in the voxel or as relative strength or concentration relative to other chemicals in the voxel. If biochemical information from multiple marker chemicals is desirable, the spectroscopic data can be further processed to isolate or identify contributions from each of the remaining marker chemicals. Their concentrations or relative strengths can also be computed from their respective spectroscopic data.

At the next step, the results of the spectroscopic analysis 346, namely the concentration or relative strengths of marker chemicals corresponding to each voxel or voxels, are displayed. The results can be displayed numerically for each measurement. The results can also be plotted as iso-concentration contours to show more visibly the distribution of concentration or strength of marker chemical or chemicals. Advantageously, the distribution of the concentration or strength also can be converted to a false color map and superimposed on the MRI image.

As will be appreciated, although the MRS sub-process 340 is described here as being performed independent of the ultrasound sub-process 304, advantageously, the ultrasound sub-process 304 can be first performed. Results from a morphological analysis, in particular, a segmentation process, can help identify a collection of voxels or the centroid, that likely represents a lesion. An envelope enclosing the volume or centroid can be generated. Subsequently, only MRS data corresponding to the voxels contained within the envelope needs to be analyzed. As another example, it may often be the case that an analysis of image data from one modality, such as ultrasonic or MRI, identifies one or more regions suspicious of cancer, for example, based on an initial assessment from data from these modalities alone. The results, however, may not be conclusive. Instead of performing an MRS procedure for an entire anatomy region or the same region as in other modalities, an MRS procedure may be performed for a much smaller region or regions, enclosing only the suspected lesions identified in other modalities. This tends to improve efficiency. Likewise, a preliminary result from MRI or MRS analysis may also provide a starting point for the data acquisition and analysis in other modalities.

Figure 3B:
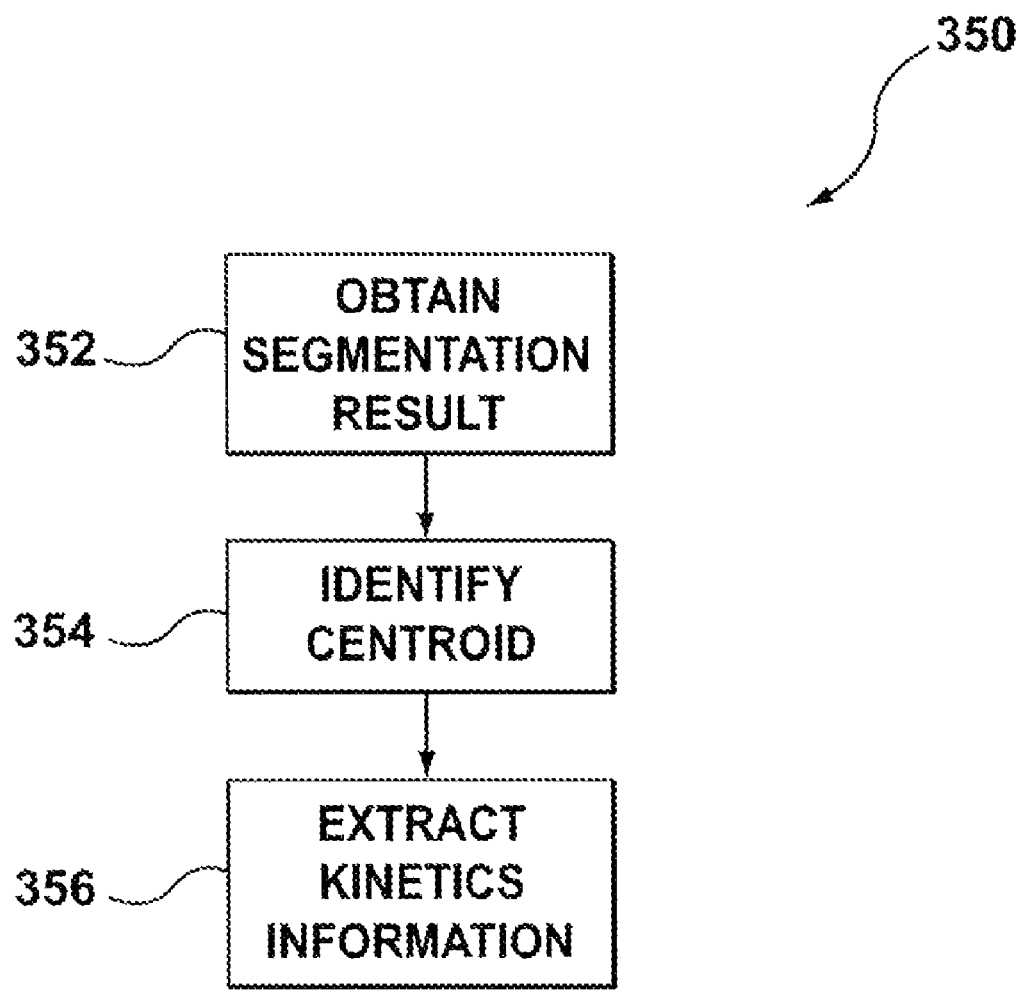
FIG. 3B is a flowchart illustrating an alternative process that is implemented by the CAD application program shown in FIG. 2, using results from one modality as inputs to another modality.

In general, a multimodality system such as the system 100 can take advantage of results from one modality and use the results as inputs to another modality to improve efficiency. As the same lesion generally can be seen in multiple modalities, results of morphological analysis performed in one modality often can be used directly in another modality. FIG. 3B illustrates in flowchart form an alternative process 350 that uses results from a morphological analysis as inputs to an MRI kinetic analysis.

As will be remembered, in a morphological analysis, first an ROI is identified and then a segmentation process is performed to identify a boundary that likely separates tumor from normal tissue. In a 3-dimensional segmentation process, the boundary is an envelope enclosing a volume or centroid that likely corresponds to a tumor. As a first step of process 350, this segmentation result is first obtained from, for example, an ultrasound module (step 352). Next, an envelope enclosing these voxels or the centroid is generated (step 354). All voxels contained within the envelope will next be analyzed to extract kinetics features.

The steps of obtaining MRI data and separating them into individual scans in a time sequence at different times T0, T1, T2, . . . are similar to that described in reference to FIG. 3 and therefore will not be described here. To extract kinetic features, images scanned at different times, such as T0 and T1, or T1 and T2, are compared. This can be implemented by, for example, first subtracting image taken at T0 from image taken at T1. Voxels having a positive value then represent voxels that have increasing contrast while voxels having a negative value represent voxels that have decreasing contrast. As an envelope is already determined from a morphological analysis, only voxels within the envelope need to be processed to extract the kinetics information. Subsequent images or scans in the time sequence are similarly processed to extract the kinetics information (step 356). Limiting the processing of kinetics information to those voxels contained inside the envelope tends to obliterate the needs of identifying voxels corresponding to a tumor in a separate run, for example, by identifying those that exhibit initial up-take and then plateau or wash-out behavior. This may also avoid the needs of processing voxels outside the envelope. Thus, efficiency as well as accuracy of the multimodality system 100 may be improved as a result.

Figure 8:
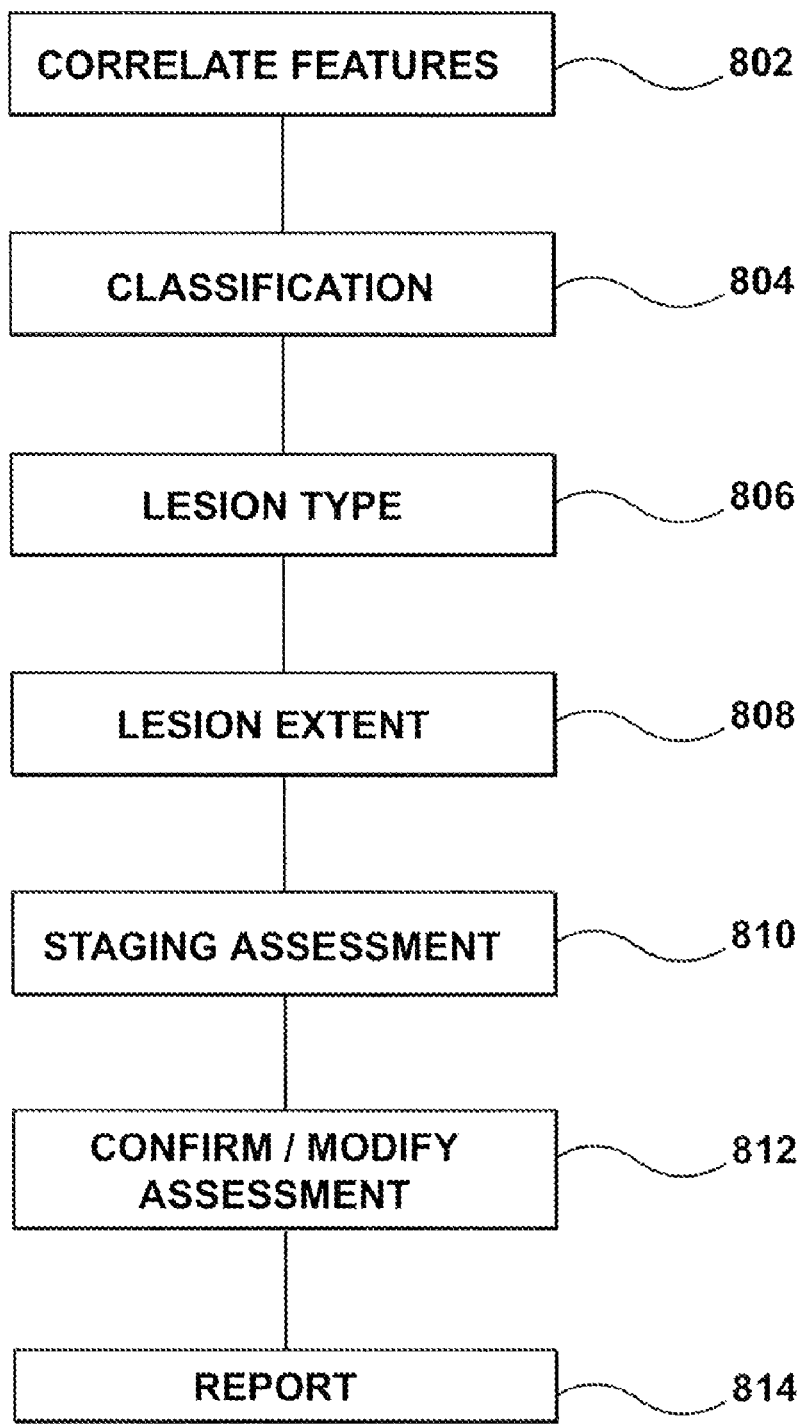
FIG. 8 is a flowchart showing a portion of the process shown in FIG. 3 for producing a consolidated result, combining morphological and kinetics features.

FIG. 8 is a flowchart showing steps followed by the consolidation decision engine 114 in a consolidated scoring process. The consolidation decision engine 114 first correlates at step 802 all features provided by all modality decision engines. For example, the shape of the lesion as determined by each modality can be correlated at this step. Each of the classification module 218, lesion-type module 220 and lesion-extent module 222 of the consolidation decision engine 114 combines the results from all modalities to classify the lesion at a classification step 804, to determine a lesion type at a type determination step 806, and to estimate the size of the lesion at an extent determination step 808.

The consolidation decision engine 114 also scores the lesion (step 810), namely, computes a diagnostic assessment, by incorporating results from all modalities. As a consolidated diagnostic assessment is produced based on results from more than one modality, confidence level in the assessment is generally increased. A rule-based process may be followed to compute a consolidated assessment. For example, features generally indicating malignancy in each modality may be assigned a score point. By summing score points obtained from all modalities, a total score can be obtained. A stage assessment can be assigned to the lesion based on the value of the final total score. Generally, a stage assessment based on features seen in one modality confirmed by features seen in another modality tends to increase the confidence in the assessment.

For example, in one implementation, the following scoring scheme is used when the consolidation decision engine 114 computes a consolidated stage assessment based on results from analysis of only MRI image data:

| Features Identified | | Points |
| --- | --- | --- |
| Lesion Morphology | | |
| Shape | round, oval, lobulated | 0 |
| | irregular | 1 |
| Margin | smooth | 0 |
| | spiculated, irregular | 1 |
| Mass enhancement | homogeneous | 0 |
| | heterogeneous, rim enhancement | 1 |
| Lesion Dynamics | | |
| Initial enhancement | increase <50% | 0 |
| | increase: [50%:100%] | 1 |
| | increase >100% | 2 |
| Kinetics | continuous enhancement | 0 |
| | plateau | 1 |
| | washout | 2 |
| BI-RADS categories | | |
| Total Score | total score = 3 | 3 |
| | total score = 4 | 4 |
| | total score: 5 to 8 | 5 |

Similarly, a statistical model may be built for image data obtained from multiple modalities, similar to that built for a single modality. For example, with results of biopsies known for a pool of image data obtained from multiple modalities, rules can be constructed to relate the presence of features seen in each of the multiple modalities to a possible stage of the tumor, with a statistical likelihood assigned to the result. This set of rules can be applied to the results from all modalities, the lesion type, extent and classification of the lesion produced by the consolidation decision engine, to compute a consolidated staging assessment of the lesion. As such a combined scoring or assessment takes into account a larger set of inputs, the result tends to be more robust. As a general rule, assessments computed from more independently obtained data tend to be more statistically reliable. Further, assessments computed from results of analyzing image data of a single modality may be strongly affected by a missing data point, for example, when an important descriptor contributing to the basis function(s) of the statistical model cannot be computed. With results from multiple modalities, results from another modality may provide the required (and missing) information, and therefore increase the confidence in the assessment computed.

However, it will be appreciated that although combining results from multiple modalities tend to improve the reliability and confidence in the assessment, there are situations where results from the analysis of one modality may be sufficient. If results from one modality are clearly suggestive, to improve performance, analysis by other modalities may be optionally skipped. For example, if an MRI kinetics analysis finds a lesion clearly cancerous, the MRI morphology analysis or morphology analysis by other modalities may be optionally skipped or suspended, unless a user specifically requests a morphology analysis. Likewise, if a morphological analysis clearly indicates a cancerous finding, an MRI kinetics analysis may be skipped or suspended. The result provided by the consolidation decision engine will then be the same as that provided by the particular modality decision engine in question.

Figure 9:
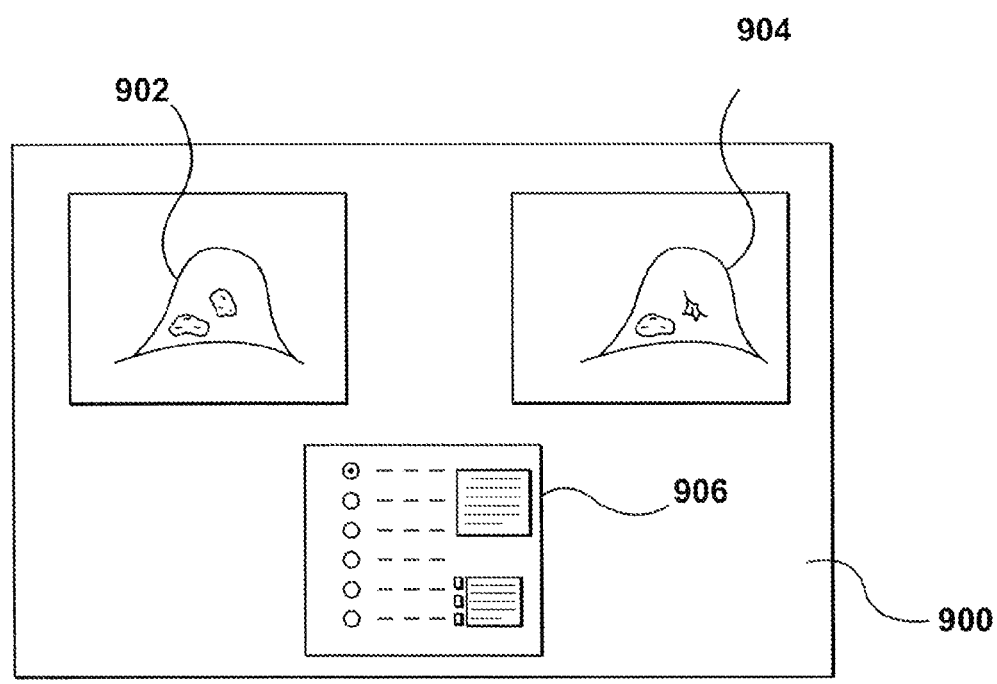
FIG. 9 shows schematically an exemplary screen display, providing to a user a side-by-side comparison of analyzed images of two modalities and a consolidated result.

The results of the consolidation engine are presented to a user for confirmation or modification (step 812). The user may be shown images from each of the modalities with features extracted superimposed on the images. The features identified by the CAD application program 106 may be annotated. Contrast variation curve 514 may be shown simultaneously to the user as well. Results identified may be pre-populated in a standard report form, following the formats established by standards such as BI-RADS MRI Lexicon or any other suitable standards. FIG. 9 shows one such possible display, which shows a first image 902 obtained from a first modality, a second image 904 from a second modality, and a report 906 containing a consolidated result, with extracted features and a consolidated assessment pre-populated.

A user, for example, a physician or a radiologist, may confirm the results as computed by the CAD application program 106, or may modify any of the automatically detected and evaluated results. An annotation module (not shown) may be provided for receiving user inputs. A user may modify or annotate the results displayed through a user interface. For example, the user may reclassify a lesion, override the classification made by the CAD application program 106, or the user may modify a staging assessment computed by the CAD application program 106. The user may also reclassify morphological or kinetics features extracted by the CAD application program 106. The CAD application program 106 will then recompute as necessary to produce a modified consolidated decision and assessment.

Once the result is confirmed by the user, a report can be generated (step 814). The generated report is similar to that generated for each individual modality, except that the result is a consolidated decision and assessment. The report contents are generally by default based on the data available in the processed images. In other words, data available in a result similar to that shown in FIG. 9 are reflected in the report. The report includes detected and classified MRI, sonographic or CT characteristics, as the case may be, and the computed and confirmed assessment, along with any annotations and comments and user modifications. Original medical images and the processed counterparts are included as well. Finally, the report contains the image findings and assessment of the radiologists (preferably, in a format complying with the relevant ACR-BIRADS classification form or forms).

A report may include identification and audit information for traceability and auditing purposes. Identification and audit information may include unique report identifier, series number, date or time stamp, namely the time and date of the study or report, patient identification number, study identification number, user ID, unique report identifier, user addition or modification of detected features, among others. Conveniently, a cryptographic module may be provided for a radiologist to digitally sign a report. A digital signature can be included and recorded for each archived instance, to provide improved audit capability and to discourage accidental modification of the reports.

Preferably, reports are archived as DICOM Secondary Capture. Annotations, comments, image processing results such as lesion boundaries and diagnosis results are archived as part of a DICOM-compliant file. A user can also save, for example, a PDF version of the report locally in a patient's instantiated directory. This facilitates easy future reference. If an instance for that composite rendering already exists in the archive for the patient, a new instance is created.

The CAD application program 106 is not limited to analysing image data taken during a single imaging session, or clinical visit. Often, it is necessary to image a patient several months apart. This may be necessary as part of regular check-ups, or as part of follow-up clinical visits after a surgery or treatment of cancer. Images from the same modality taken during different visits may need to be analyzed and compared with each other. For example, it may be necessary to determine whether a detected benign lesion has become malignant. Alternatively, it may be necessary to determine whether a malignant lesion has become smaller or stopped growing after treatment.

Figure 10:
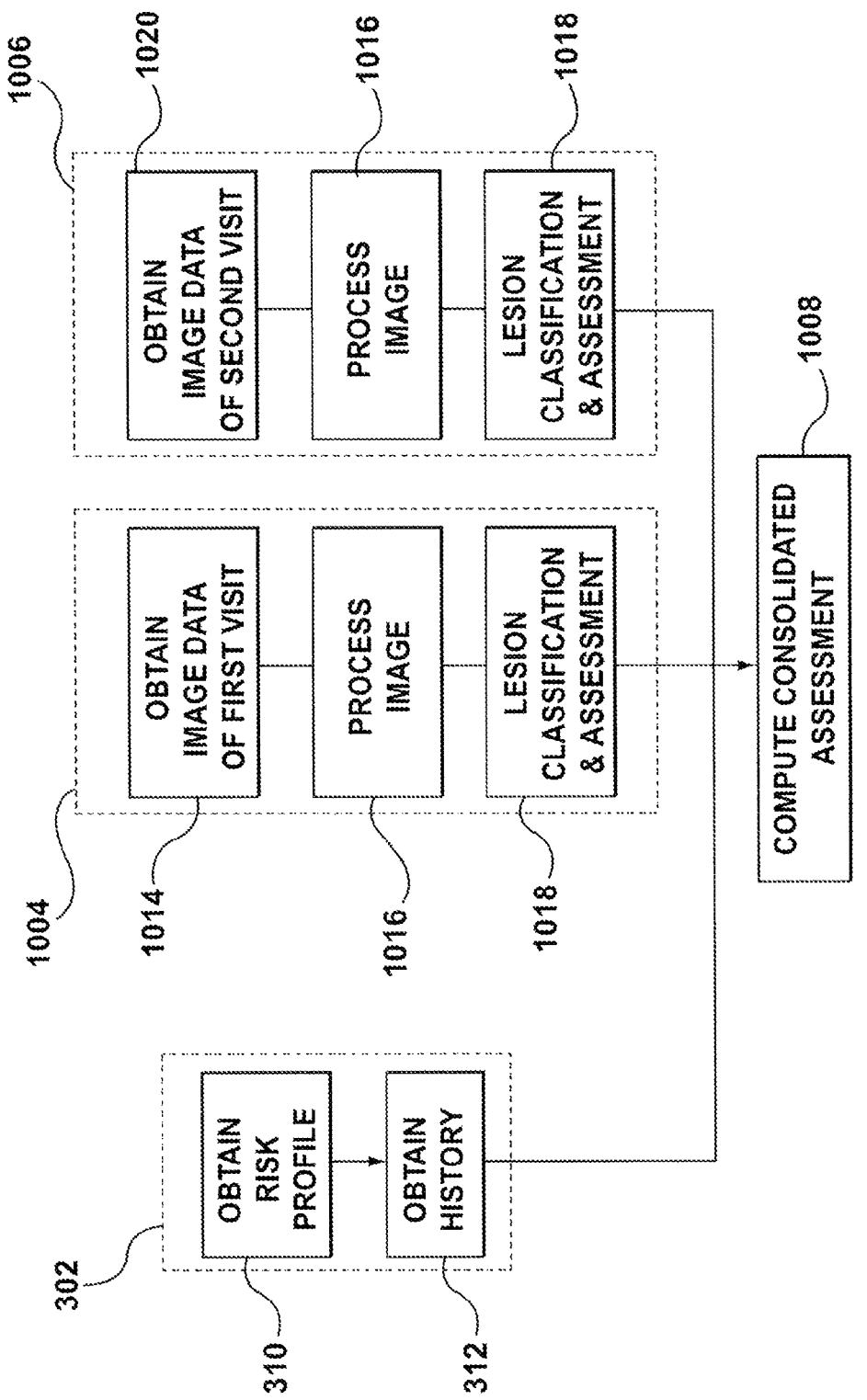
FIG. 10 shows a process modified from that shown in FIG. 3 for processing images from the same modality, taken at different times.

FIG. 10 shows a process for processing images from the same modality, acquired at different times. This is a process modified from that shown in FIG. 3. FIG. 10 also shows three parallel sub-processes, namely, a patient data retrieval sub-process 302, a first morphology sub-process 1004, and a second morphology sub-process 1006. The sub-processes are shown as parallel processes as well. In this modified process, the first and second morphology sub-processes 1004, 1006 are essentially the same, with one exception. At the start of sub-process 1004, image data of the first visit are retrieved (step 1014). At the start of sub-process 1006, image data of the second visit are retrieved (step 1020). The processing of the image data (step 1016) and lesion classification and assessment (step 1018) are the same for both sub-processes 1004, 1006, and are essentially the same as that described in connection with the ultrasound sub-process 304 as well. The sub-processes 1004, 1006 therefore will not be described in detail here.

In the final step 1008, the consolidation decision engine 114 computes a consolidated assessment of the lesion in the image data of the second visit, incorporating features extracted from image data of first visit. As the image data are obtained at different times, the same lesion, even if visible in both image data, tends to be at different stages and will need to be matched to imagined patterns seen in images acquired during the two visits. The consolidation decision engine 114, when correlates the lesion, will need to take into account of the time difference. Time projection of development of the lesion seen in the image data of the first visit may be necessary. Once the features of the lesion in both sets of image data are correlated, a consolidated assessment can be evaluated as before. However, it will be understood that a different model or a different set of rules may be required to correlate features identified in a lesion imaged at different times. Results for each individual set of image data can also be presented to a user, such as a radiologist in a side-by-side comparison. The side-by-side comparison can include results such as lesion type and extent as well as its classification. Such a comparison may assist a physician to assess either the development of the lesion or the effect of the treatment.

Various embodiments of the invention have now been described in detail. Those skilled in the art will appreciate that numerous modifications, adaptations and variations may be made to the embodiments without departing from the scope of the invention. Since changes in and or additions to the above-described best mode may be made without departing from the nature, spirit or scope of the invention, the invention is not to be limited to those details but only by the appended claims.

What is claimed is:

1. A method of analyzing a plurality of medical image data of a region in an anatomy and detecting abnormalities in the region, at least a set of the plurality of medical image data containing temporal information responsive to administering of a contrast enhancement agent, the method comprising the steps of:
    obtaining the plurality of medical image data;
    identifying from the plurality of medical image data a set of data points representing a possible lesion in said region;
    extracting from the plurality of medical image data features associated with said set of data points, said features including at least two sets of a set of morphological features, a set of kinetics characteristics of the temporal information, and a set of biochemical characteristics;
    combining features from said at least two sets of features to arrive at a consolidated classification, a consolidated lesion type and a consolidated lesion extent and computing a staging assessment from a combination of said consolidated classification, said consolidated lesion type and said consolidated lesion extent;
    computing an initial diagnostic assessment of said possible lesion from said at least two sets of features, said initial diagnostic assessment incorporating information from said staging assessment; and
    providing said initial assessment to a user for evaluation.

2. The method of claim 1, further comprising the steps of:
    receiving a modification to said at least two sets of features from the user, and
    computing a modified assessment, said modified assessment being computed further incorporating said modification; and
    providing said modified assessment to the user for further evaluation.

3. The method of claim 1, wherein the kinetics characteristics are extracted from a contrast variation curve corresponding to time-dependent local contrast variation in a subset of said set of data points.

4. The method of claim 3, wherein the kinetics characteristics include a classification of the contrast variation curve into one of continued enhancement, plateau and washout types.

5. The method of claim 3, wherein the step of extracting the kinetics characteristics includes identifying an envelope enclosing the possible lesion and wherein the contrast variation curve is extracted by identifying said time-dependent local contrast variation in data points enclosed within said envelope.

6. The method of claim 3, further comprising the step of obtaining a plurality of rules associating the set of morphological features, the set of kinetics characteristics of the temporal information, and the set of spectral characteristics with possible diagnosis, said initial assessment and said modified assessment being computed from said plurality of rules and said at least two sets of features.

7. The method of 1, wherein the plurality of medical image data includes medical image data acquired from at least two modalities, said computation and re-computation further comprising the steps of:
    for each modality of said at least two modalities, computing a modality decision from features extracted from medical image data of said each modality,
    correlating said modality decisions in said computation and re-computation.

8. The method of claim 2, wherein the plurality of medical image data includes medical image data acquired from at least two modalities, said computation and re-computation further comprising the steps of:
    for each modality of said at least two modalities, computing a modality decision from features extracted from medical image data of said each modality,
    correlating said modality decisions in said computation and re-computation.

9. The method of claim 1, wherein the biochemical characteristics are extracted from a spectral analysis of an MRS subset of said set of data points.

10. The method of claim 9, wherein the biochemical characteristics include at least a concentration distribution of a marker chemical.

11. The method of claim 9, wherein the biochemical characteristics include at least relative strength of two or more marker chemicals obtained from a spectroscopic analysis.

12. The method of claim 1, wherein the plurality of medical image data includes at least a set of image data selected from the group of X-ray image data, ultrasound image data, MRI image data, MRS data, CT image data, PET image data, PET/CT image data, digital tomosynthesis image data, and nuclear image data.

13. The method of claim 1, further comprising the step of retrieving patient risk profile information, wherein said evaluation process incorporates said patient risk profile information.

14. A system for analyzing a plurality of medical image data of a region in an anatomy, at least a set of the plurality of medical image data containing temporal information responsive to administering of a contrast enhancement agent, the system comprising:
    an image data module for retrieving the plurality of medical image data;
    a morphology module for identifying a possible lesion in said medical image data and extracting and classifying morphological features associated with said possible lesion;
    a kinetic module, said kinetics module extracting from the plurality of medical image data kinetics characteristics of the temporal information associated with said possible lesion;
    a spectroscopic analysis module, said spectroscopic analysis module extracting from the plurality of medical image data biochemical characteristics relating to one or more marker chemicals;
    a consolidation decision engine, said consolidation decision engine receiving said extracted and classified morphological features from said morphology module, said extracted kinetics characteristics of said temporal information from said kinetics module, and said biochemical characteristics from the spectroscopic analysis module, combining features from at least two sets of a set of said extracted and classified morphological features, a set of said extracted kinetics characteristics, and a set of said biochemical characteristics to arrive at a consolidated classification, a consolidated lesion type and a consolidated lesion extent, computing a staging assessment from a combination of said consolidated classification, said consolidated lesion type and said consolidated lesion extent, and computing an initial diagnostic assessment of said possible lesion from said at least two sets of features, said initial diagnostic assessment incorporating information from said staging assessment; and a graphical user interface for displaying at least a portion of said plurality of medical image data along with said initial diagnostic assessment for user evaluation and modification.

15. The system of claim 14, further comprising:
a morphology decision engine for deriving a morphology assessment from said extracted and classified morphological features;
a kinetics decision engine for deriving a kinetics assessment from said extracted kinetics characteristics; and
a spectroscopic analysis decision engine for deriving a spectroscopic assessment from said biochemical characteristics,
wherein said consolidation decision engine correlates and incorporates said morphology assessment, said kinetics assessment and said spectroscopic assessment in its computation.

16. The system of claim 14, further comprising an annotation module for receiving through said graphical user interface a modification to at least one of said extracted and classified morphological features, said kinetics characteristics and said biochemical characteristics, wherein said consolidation decision engine re-computes a modified diagnostic assessment upon receiving said modification.

17. The system of claim 14, wherein the kinetics module comprises a curve construction module for constructing a contrast variation curve corresponding to time-dependent local contrast variation in a subset of said set of data points and a kinetics analytic module for extracting said kinetics characteristics from said contrast variation curve.

18. The system of claim 14, wherein the image data module is configured for retrieving medical image data of multiple modalities and said consolidation decision engine comprises modules for receiving morphological features and kinetics characteristics extracted from medical image data of each one of said multiple modalities.

19. The system of claim 18, wherein the multiple modalities include X-ray image data, ultrasound image data, MRI image data, MRS data, CT image data, PET image data, PET/CT image data, digital tomosynthesis image data, and nuclear image data.

20. The system of claim 17, wherein the kinetics analytic module is configured to classify the contrast variation curve into one of continued enhancement, plateau and washout types and wherein said kinetics characteristics include said curve type.

21. The system of claim 14, further comprising:
a patient risk profile module for retrieving patient risk profile information from a data base; and
a patient history module for retrieving patient history information;
wherein said evaluation of said assessment incorporates said patient risk profile information and said patient history information.

22. A system for analyzing medical image data of a region in an anatomy, the medical image data being acquired from a plurality of modalities, the system comprising:
an image data module for receiving the medical image data;
a plurality of image processing modules, each for processing image data acquired from one of said plurality of modalities, said each module identifying a possible lesion in said medical image data and extracting and classifying a set of modality characteristics associated with said possible lesion;
a plurality of modality decision engines, each of said modality decision engines computing a modality diagnosis assessment of said possible lesion for a modality of said plurality of modalities from said set of modality characteristics associated with the modality;
a consolidation decision engine, said consolidation decision engine combining said modality diagnosis assessments and computing an initial diagnostic assessment of said possible lesion from said modality diagnosis assessments; and
a graphical user interface for displaying at least a portion of said medical image data along with said initial diagnostic assessment for user evaluation and modification.

23. The system of claim 22, wherein at least part of the medical image data contains temporal information responsive to administering of a contrast enhancement agent to the patient and said set of modality characteristics includes at least one of a set of morphological features and a set of kinetics characteristics of the temporal information.

24. The system of claim 22, wherein at least part of the medical image data contains spectroscopic information obtained from an MRS data acquisition, and said set of modality characteristics includes at least biochemical characteristics of one or more marker chemicals.

25. The system of claim 24, wherein said biochemical characteristics include at least a concentration distribution of said one or more marker chemicals.

26. The system of claim 22, wherein, in identifying the possible lesion, one of the plurality of image processing modules receives input from at least one of another image processing module of the plurality of image processing modules and another modality decision engine of the plurality of modality decision engines.

27. The system of claim 26, wherein said input is a reference to a set of lesion data points corresponding to the possible lesion.

* * * * *